(12) United States Patent
Drennan

(10) Patent No.: US 10,638,969 B2
(45) Date of Patent: May 5, 2020

(54) WIRELESS PRESSURE ULCER ALERT METHODS AND SYSTEMS THEREFOR

(71) Applicant: DM SYSTEMS INC., Evanston, IL (US)

(72) Inventor: Denis Burke Drennan, Evanson, IL (US)

(73) Assignee: Walgreens Health Solutions, LLC, Lake Forest, IL (US)

( * ) Notice: Subject to any disclaimer, the term of this patent is extended or adjusted under 35 U.S.C. 154(b) by 795 days.

(21) Appl. No.: 14/936,596

(22) Filed: Nov. 9, 2015

(65) Prior Publication Data

US 2016/0135731 A1    May 19, 2016

Related U.S. Application Data

(60) Provisional application No. 62/077,393, filed on Nov. 10, 2014.

(51) Int. Cl.
*A61B 5/00* (2006.01)

(52) U.S. Cl.
CPC ............ *A61B 5/447* (2013.01); *A61B 5/0004* (2013.01); *A61B 5/7282* (2013.01); *A61B 5/742* (2013.01); *A61B 5/7405* (2013.01); *A61B 5/746* (2013.01); *A61B 2560/0475* (2013.01); *A61B 2562/0247* (2013.01)

(58) Field of Classification Search
CPC ..................................................... A61B 5/447
See application file for complete search history.

(56) References Cited

U.S. PATENT DOCUMENTS

| 7,378,975 B1 | 5/2008 | Smith et al. |
| 8,535,246 B2 | 9/2013 | Drennan et al. |
| 8,675,059 B2 | 3/2014 | Johnson et al. |

(Continued)

FOREIGN PATENT DOCUMENTS

WO    2013056225    4/2013

OTHER PUBLICATIONS

European Search Report dated May 29, 2018; EP Application No. 15859482.0.

*Primary Examiner* — Daniel L Cerioni
*Assistant Examiner* — Yasmeen S Warsi
(74) *Attorney, Agent, or Firm* — Hartman Global IP Law; Gary M. Hartman; Domenica N. S. Hartman

(57) ABSTRACT

Pressure monitoring methods and systems for warning a patient or caregiver that soft tissue pressure has exceeded some predetermined level that over time would necessitate moving the patient to prevent or at least reduce a risk of soft tissue damage. The methods and systems entail the use of a pressure sensing unit adapted to be applied to or near a surface of the patient's body, and a sensor associated with the sensing unit to generate electrical outputs corresponding to soft tissue pressure sensed at the surface. The electrical outputs are wirelessly monitored over a preselected time period to generate a cumulative output signal based on the electrical outputs and corresponding to whether or not the soft tissue pressure has exceeded a predetermined pressure level during the preselected time period. An alarm is generated if the cumulative output signal exceeds a predetermined cumulative threshold until the soft tissue pressure drops below the predetermined pressure level.

14 Claims, 29 Drawing Sheets

(56) References Cited

U.S. PATENT DOCUMENTS

| | | | |
|---|---|---|---|
| 2005/0165284 A1* | 7/2005 | Gefen | A61B 5/015 600/300 |
| 2008/0208063 A1 | 8/2008 | Brauers et al. | |
| 2010/0198022 A1* | 8/2010 | Vuillerme | A61B 5/1036 600/301 |
| 2010/0268122 A1* | 10/2010 | Drennan | A61B 5/103 600/587 |
| 2011/0263950 A1 | 10/2011 | Larson et al. | |
| 2014/0153724 A1* | 6/2014 | Kim | H04L 63/0428 380/270 |

* cited by examiner

OUTCOME ENTRY

DATE: 04/30/2014
PATIENT ID: 12345
BIRTH DATE: 02/10/1960
FLOOR / ROOM: 4 / 304

Please record the pressure ulcer outcomes below.

● No Pressure Ulcers Occurred On Any Location

● Pressure Ulcer Occurred  Anatomic Location [R HEEL ▼]  Pressure Ulcer Level [GRADE I ▼]

● Pre-Existing Pressure Ulcer: HEALING  Anatomic Location [R HEEL ▼]  Pressure Ulcer Level [GRADE I ▼]

● Pre-Existing Pressure Ulcer: HEALED  Anatomic Location [R HEEL ▼]

SAVE
CANCEL

HELP

FIG. 9

Admin Screen - Facilities

| Admin | Patient Info | Monitor | ? |
|---|---|---|---|
| 94 | 96 | 98 | 84 |

Pantone 292 C, Pantone 292 C, Pantone 292 C, Pantone 292 C

Sign Out — Pantone 2727 C

Pantone 2727 C

100 →

The following is a list of organizations under your parent organization: Hospital123

Address

Street, City, State, Zip

Facility Name

Hospital Name

Units/Floors

Floor 2 ICU

Add New

Pantone 2727 C

Cancel — Pantone 7408 C

Admin Only

FIG. 18

Patient Screen

| Admin | Patient Info | Monitor |
|---|---|---|

Name: First Last
Unit/Floor: HF1
ID#: 1234
Gender: Male
Room/Bed: Room 2024
DOB: 01/01/01
Weight: 96
Diagnosis: Diabetes — Add New — (Paralysis, Neuropathy, Prior Ulcers, Diabetes, Heart Failure, Cerebrovascular, Post Operative, Hip Fracture, Peripheral Vascular Disease, Hip Fracture, Other)
Mobility: Independent (Independent, 1 Person Assist, 2 Person Assist, Total Dependent)
Bed Type: Plain Mat (Plain Mat, Mat overlay, Low air Loss, Air Fluidized, Foam Mattress, Lat Rotation, Other)
Braden: Severe 9 (Not Applicable, Severe 9, High 10-12, Moderate 13-14, Mild 15-18)
PURS: Non Applicable (Not Applicable, Very High Risk 6-8, High Risk 4-5, Med 3, Low 0-2)
Existing PU: Yes/No — View/Edit PUs
New PU: Yes/No — View/Edit PUs
Report: View Report Note:
- When user hits Monitor Patient Button, it goes to the Monitor page
- For Diagnosis, you can keep adding new conditions since a new drop down is always added after a drop down has been specified
- Patient info should be centered in screen
- If Existing/New PU is a Yes for the first time, it takes you to the PU Status screen

FIG. 24

Patient Screen PU Status

| Admin | Patient Info | Monitor |
|---|---|---|
| Pantone 292 C | Pantone 292 C | Pantone 292 C |
| 94 | 96 | 98 |

Name, ID, DOB, Date, Time, Floor, Room, Bed

| Status | Location | Stage/Category | Date | Time |
|---|---|---|---|---|
| Existing PU | Skull | I | N/A | N/A |
| New PU | Skull | II | 1/1/1 | 12:34 |
| Add New | | | | |

Notes
- Location Drop Down: Skull, Upper Spine, Left Elbow, Right Elbow, Sacrum, Left Ischia, Right Ischia, Left Hip, Right Hip, Left Heel, Right Heel
- Stage/Category Drop Down: I, II, III, IV, Unstageable, Deep Tissue Injury, Diabetic
- Date/Time only editable if a new PU Sign Out — Pantone 2727 C 84 — Pantone 292 C (?)

Pantone 2727 C — Cancel

FIG. 25

WIRELESS PRESSURE ULCER ALERT METHODS AND SYSTEMS THEREFOR

BACKGROUND OF THE INVENTION

The present invention generally relates to equipment and procedures for use with health care patients. More particularly, the present invention encompasses methods and equipment for monitoring soft tissue pressure to which a patient may be subjected, with the intent of reducing the risk of soft tissue damage.

Pressure (decubitus) ulcers, commonly known as bedsores, present a serious problem to bedridden and wheelchair-confined patients. Prolonged pressure from a patient's body weight upon bony prominences is the most common cause of pressure ulcers. Prevention of and care for a preexisting pressure ulcer typically include treatment plans that involve relieving pressure on the exposed area by positioning and maintaining the patient off susceptible areas and any preexisting pressure ulcers, and minimizing localized pressure through the use of gel pads and similar types of products capable of absorbing and/or distributing pressure. However, such approaches can be insufficient if caregivers are unaware that a patient has shifted his/her weight onto prominences that are prone to pressure ulcers.

There are a wide variety of pressure sensors in the industrial and medical markets, some of which have found use in monitoring pressure ulcers. Notable examples include those that use air and fluid displacement techniques, as well as electromechanical analog devices. Many of these sensors are very portable and can be used to measure pressures at various locations of a patient at any point in time. There are also sheets of pressure sensors used primarily for research that give color-coded results from computer programs. The latter sensor type has been particularly used by manufacturers and some healthcare facilities to identify maximum tissue pressures under bed and wheelchair patients' skin areas. There are also a number of pressure monitoring devices, for example, the Oxford Pressure Monitor MKII with 12 Sensor system available from the Talley Group, Ltd., and the Pressure Alert system available from Cleveland Medical Devices, Inc.

U.S. Pat. No. 8,535,246 to Drennan et al. discloses a pressure monitoring system for warning a patient or caregiver that soft tissue pressure has exceeded some predetermined level that over time would warrant moving the patient to prevent or at least reduce a risk of soft tissue damage. The system entails the use of a pressure sensing unit that generates electrical outputs corresponding to soft tissue pressure sensed at a surface of the patient's body. In preferred embodiments, the system monitors the electrical outputs over a preselected time period and generates a cumulative output signal based on the electrical outputs and corresponding to whether or not the soft tissue pressure has exceeded a predetermined pressure level during the preselected time period. The system may generate audible and/or visual warnings if the cumulative output signal exceeds a predetermined cumulative threshold until the soft tissue pressure drops below the predetermined pressure level.

Although the Drennan et al. system provides many benefits, further improvements in pressure monitoring systems would be desirable.

BRIEF DESCRIPTION OF THE INVENTION

The present invention provides pressure monitoring methods and systems suitable for providing a warning to a patient or caregiver that soft tissue pressure has exceeded some predetermined level that, over a sufficient period of time, would necessitate that the patient should move or be moved to prevent or at least reduce the risk of soft tissue damage. The method and system may include improved sensors, warning systems, and/or data recording systems over existing pressure monitoring systems.

According to one aspect of the invention, a pressure monitoring system includes a pressure sensing unit adapted to be applied on or near a surface of the patient's body that is susceptible to damage from soft tissue pressure. The pressure sensing unit comprises at least one sensor that generates electrical outputs corresponding to soft tissue pressure sensed by the sensor at the surface of the patient's body. The system includes means for wirelessly monitoring a plurality of the electrical outputs generated by the sensor. A counter associated with the monitoring means generates a counter value that increases from an initial value while the soft tissue pressure exceeds a predetermined pressure level, and decreases toward the initial value while the soft tissue pressure does not exceed the predetermined pressure level. According to certain preferred aspects, the counter value increases at a first ratio relative to actual elapsed time and the counter value decreases at a second ratio relative to actual elapsed time, and the second ratio is less than the first ratio. The system also preferably has means for generating an alarm while the counter value exceeds a predetermined counter value.

According to another aspect of the invention, a method of monitoring pressure and reducing the risk of soft tissue damage to a patient includes applying a pressure sensing unit to or near a surface of the patient's body that is susceptible to damage from soft tissue pressure. The pressure sensing unit comprises a sensor that generates electrical outputs corresponding to soft tissue pressure sensed by the sensor at the surface of the patient's body. A plurality of the electrical outputs generated by the sensor is wirelessly monitored. According to certain preferred aspects, a counter value is generated that increases from an initial value while the soft tissue pressure exceeds a predetermined pressure level, and decreases toward the initial value while the soft tissue pressure does not exceed the predetermined pressure level. The counter value increases at a first ratio relative to actual elapsed time and the counter value decreases at a second ratio relative to actual elapsed time, and the second ratio is preferably less than the first ratio. An alarm is preferably generated while the counter value exceeds a predetermined counter value.

A significant advantage of this invention is that pressure monitoring systems and methods of this invention are adapted to provide a warning to a patient or caregiver that specifically takes into consideration the actual risk of soft tissue damage to the patient based on the soft tissue pressure level, the duration the pressure has been applied, and any interruptions of the applied pressure. In particular, the system is adapted to warn the patient and/or caregiver if a sensed soft tissue pressure level exceeds a predetermined level and whose cumulative effect would warrant if not necessitate that the patient should move or be moved to prevent further soft tissue damage. In addition, pressure monitoring systems wireless sensor arrangement in which multiple sensors may be secured to a patient without restricting movements of the patient in a bed, and would not be required to be removed prior to moving the patient to or from a bed. Another significant aspect of the invention is the ability to monitor pressure, generate a signal or alarm (e.g., audible, visual, or vibration) in the event that pressure exceeds a pressure threshold, particularly for a predetermined period of time, and continue such a signal or alarm until the cause of the excessive pressure event has been appropriately addressed by the patient or a caregiver. In some cases, an audible, visual or vibrational signal or alarm can inform the patient of the specific anatomical location that must be moved. Also, the system may notify the caregiver of the warning on a mobile device, in which case the caregiver may be notified even if not currently in the room with the patient.

Other aspects and advantages of this invention will be better appreciated from the following detailed description.

BRIEF DESCRIPTION OF THE DRAWINGS

FIG. 9 represents an outcome entry that may be completed by a caregiver or patient after the patient has been monitored with the system of FIG. 1.

FIG. 18 represents an embodiment of a facilities module screen accessed through the administrative screen of FIG. 17.

FIG. 24 represents an embodiment of patient information details screen accessed through the patient screen of FIG. 23.

FIG. 25 represents an embodiment of a PU (pressure ulcer) status screen accessed through the patient information details screen of FIG. 24.

DETAILED DESCRIPTION OF THE INVENTION

Figure 1:
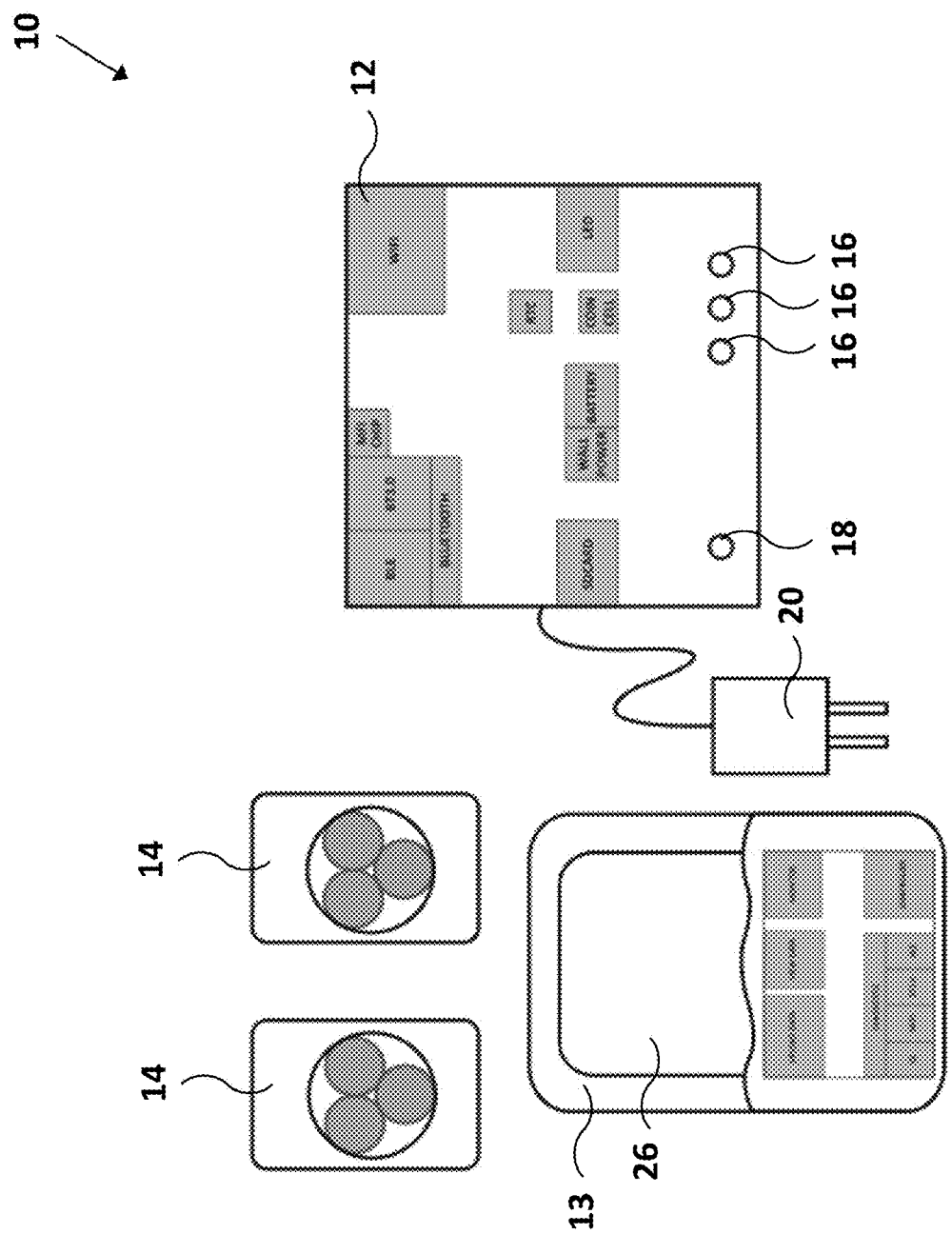
FIG. 1 schematically represents components of a pressure monitoring system in accordance with an embodiment of this invention.

The present invention provides a pressure monitoring system whose primary function is to monitor a patient that is reclined or otherwise in a position that may result in the patient's weight applying pressure to an area of the patient's body that is susceptible to pressure ulcers, such as soft tissue overlying a bony prominence. The pressure monitoring system further operates to correlate soft tissue pressure levels with time to warn if an applied pressure has met certain pressure and time thresholds that, in combination, are likely to result in or exacerbate a pressure ulcer. Because a soft tissue pressure level of 30 mmHg (about 4000 Pa) has become universally accepted as a critical threshold pressure level in the development of pressure ulcers, a particularly suitable target value for the threshold pressure used by the system is believed to be about 30 mmHg, though more broadly threshold pressures within a range of about 30 and about 40 mmHg (about 4000 to about 5300 Pa) are believed to be practical and acceptable, and future medical research may suggest that critical pressure levels exist outside this range. A variety of time periods may be utilized as suitable time thresholds (for example, ten, thirty, or sixty minutes) that can be selected by a caregiver. The selected time threshold serves as a time period during which the number and duration of pressure excursions above the threshold pressure level are used to perform an assessment. If warranted, the assessment concludes with an alarm (e.g., audible, visual, vibration, etc.) that alerts caregivers and, if conscious and sufficiently alert, the patient so that the patient can be repositioned in a timely manner to avoid or at least reduce the risk of a pressure ulcer. The type and level of the alarm can be selected to induce a conscious patient to move themselves in order to relieve the soft tissue pressure and stop the alarm, saving both tissue damage and the valuable time of a caregiver. As such, the monitoring system can also be viewed as a training device for patients who are cognitively aware and capable of repositioning themselves without assistance.

A significant feature of the invention outlined above is believed to be the correlation of pressure and time, combined with an alarm that is responsive to this correlation in order to reduce the likelihood that a patient will remain on fragile tissue or a pre-existing ulcer longer than is deemed to be clinically allowable. A preferred feature of the system is the ability to accurately detect soft tissue pressure above the threshold pressure level, monitor the duration over which the pressure is above this threshold, and then either sound the alarm if the pressure remains above the threshold for the preselected time period or reset the time period if the soft tissue pressure is adequately relieved before the preselected time period is exceeded.

In particularly preferred embodiments, the system utilizes a counter that is initiated to generate a cumulative output whose initial value is zero (e.g., time units such as seconds or minutes), begins to increase once the pressure threshold is exceeded, but decreases back toward zero time units if the soft tissue pressure drops below the threshold. A preferred aspect of the invention is that the counter value increases at a first ratio relative to actual elapsed time, and decreases at a second ratio relative to actual elapsed time, and wherein in preferred embodiments the second ratio is less than the first ratio. For example, an increase in the counter value may occur at a first predetermined ratio of 1:1 relative to actual elapsed time, whereas a decrease in the counter value occurs at a second predetermined ratio of less than 1:1 relative to actual elapsed time, for example, at a ratio of 1:4, in other words, one counter minute for every four actual minutes that have elapsed after the soft tissue pressure has dropped below the threshold. In this manner, the system operates to avoid soft tissue damage by taking into consideration not only how long the soft tissue pressure persisted above the pressure threshold, but also the elapsed time following a corrective measure taken prior to the end of the preselected time period if the corrective measure results in the soft tissue pressure dropping below the pressure threshold. Preferably, the counter immediately resumes and its value again increases at the first predetermined ratio (e.g., a 1:1 ratio to actual time) if the patient moves to a position that resumes the excessive soft tissue pressure condition. Suitable electrical circuitry and timers for performing the counter function are commercially available and well within the capabilities of those skilled in the art, and therefore will not be discussed in any detail here.

In view of the above, it can be appreciated that optimal performance of the monitoring system will be achieved if the preselected time period is based on pressure ulcer risk assessments made by appropriately trained medical personnel. The monitoring system may also be equipped to retain clinical information regarding recent soft tissue pressure levels and durations, which can be useful to more fully assess a patient's history relating to the risk of soft tissue damage. Such historical data, which may further include patient clinical information and alarm events, can be retained by the system, such as with a memory card or memory device of a type commonly used in consumer electronics, or through a wireless or cable network connection to an external database. This information can then be downloaded to a personal computer or the like, printed and made a part of a patient's medical record, as well as downloaded onto electronic media for inclusion in a patient's hard or electronic medical record.

FIG. 1 is a schematic representation of one nonlimiting embodiment of a pressure monitoring system 10 of the present invention. The system 10 is shown as including a converter 12, a tablet 13 (with a partial cutaway view showing internal components), and two pressure sensing units 14 adapted to monitor soft tissue pressure at one or more surface regions of a patient's body that are susceptible to damage from soft tissue pressure. At least two sensing units 14 are preferably provided to allow multiple areas of concern to be simultaneously monitored, though it is foreseeable that a single sensing unit 14 may be sufficient under some circumstances. The sensing units 14 are connected to the converter 12 through wireless connections. The sensing units 14 may be applied directly to a patient's skin, integrated into a patient's clothing, and/or integrated into the bedding on which the patient lies, for example, into a large bed pad that covers a portion of the patient's bed. The system 10 is shown as including a power converter 20 of any suitable type capable of delivering an appropriate power level for electronics within the converter 12. The system 10 is also preferably capable of operating from battery power, such as for mobile uses (e.g., wheelchairs, bicycles, etc.) or in the event of a power outage. For this purpose, the converter 12 may contain a backup battery or may be adapted to run off a battery of a self-propelled wheelchair or other powered device.

The converter 12 is preferably configured to wirelessly connect to the tablet 13 or similarly capable device, such as a personal computer, mobile phone, or types of mobile devices that might be referred to as personal digital assistants (PDA). The tablet 13 may be any type of tablet computer device suitable for wirelessly connecting with and sharing data with the converter 12. The tablet 13 may use any operating system, for example, Google Android® or Apple iOS®, operating a software application installed thereon configured to interface with the converter 12 and interpret data provided therefrom. The tablet 13 also preferably displays and provides functionality suitable for an operator to interact with the software application. The tablet 13 of FIG. 1 is represented as having a display 26, preferably a touchscreen as common with current tablets in the art. With the software application installed on the tablet 13, the display 26 may provide a status of the system 10 which can be conveyed to an operator, and with which the operator can configure the operation of the converter 12, including the selection of the time period as discussed above. The tablet 13 is preferably configured with a graphical user interface (GUI) that guides the user from screen to screen on the display 26 during setup of the system, such as when entering patient information and setting warning levels and thresholds, as well as for the purpose of controlling the download or transfer of information to or from the converter 12 (FIGS. 4A-5B). The display 26 preferably displays the preselected time period, whether the pressure being sensed by one or more of the sensing units 14 exceeds the pressure threshold, and optionally the actual pressure being sensed. According to a particularly preferred aspect of the invention, the software application is also adapted to display an elapsed time progress bar 52 (FIGS. 5A and 5B) on the display 26, which displays the total accumulated elapsed time that any one or more of the sensing units 14 has sensed a pressure exceeding the pressure threshold. The elapsed time progress bar 52 displayed on the display 26 also preferably ramps upward and backward at the same rate as the counter, providing a visual signal that alerts a caregiver as to any accumulating time condition that may exacerbate the pressure ulcer.

Figure 2:
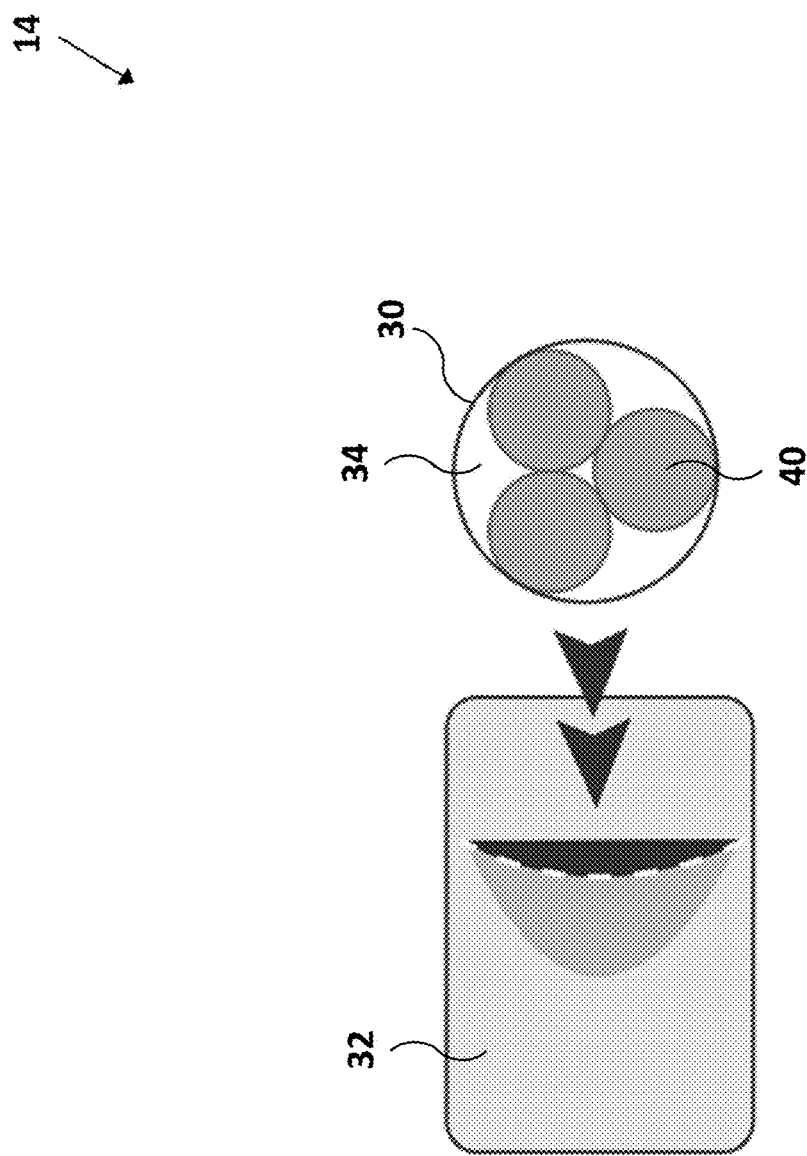
FIG. 2 represents sensors and a carrier of a pressure sensing unit of FIG. 1.

A more detailed view of an embodiment of a pressure sensing unit 14 is shown in FIG. 2, and represents the assembly 14 as having a sensor 30 centrally located within a carrier 32, for example, fabricated from one or more dressing materials. The carrier 32 may be formed of a foam, hydrocolloid, alginate self-adherent dressing or other suitable material, and is preferably sized and shaped for the particular anatomic location on the patient where the pressure sensing unit 14 will be located. As such, alternative shapes may be used and preferred for the pressure sensing unit 14 and/or its carrier 32, for example, to cover curved body structures such as the heel. The pressure sensing unit 14 is depicted in FIG. 2 as including three pressure transducers 40 located on a printed circuit board (PCB) 34. The PCB 34 and pressure transducers 40 are represented as being placeable within a pocket formed in the carrier 32. The sensor 30 may further comprise a battery and components (not shown) suitable for communicating with the transducers 40 and wirelessly communicating with the converter 12. According to a preferred aspect of the invention, the sensor 30 includes a replaceable battery in a holder (not shown) providing the ability to recycle the transducers 40 rather than discarding them.

The sensor 30 is adapted to generate electrical outputs corresponding to pressure, and particularly to soft tissue pressure to which the transducers 40 are subjected when placed on or near a patient's body. In order for the system 10 to provide a reliable risk assessment, a feature of the invention is the type of transducers 40 used and their accuracy at the relatively low pressures of interest. While embodiments of the present invention may use variable output pressure transducers, including FlexForce® load sensors available from Tekscan, Inc., transducers comprising pressure-sensitive contacts, effectively operating as binary (on-off) switches, have also been determined to be well suited for use in the pressure monitoring system 10 of this invention. In embodiments of the transducers 40 utilizing a force or pressure-sensitive contact, for each occurrence in which the pressure (or equivalent force) sensed by a transducer 40 exceeds the pressure threshold, an electrical contact will close and complete (short) an electrical circuit therein, causing the transducer 40 to generate an identical output level regardless of what extent the soft tissue pressure may exceed the pressure threshold. The sensor 30 produces an electrical output signal generated by the completed electrical circuit that can be wirelessly transmitted to the converter 12. If any one of the transducers 40 in the sensor 30 exceeds the pressure threshold, the electrical output signal is preferably transmitted to the converter 12 to indicate a risk of an ulcer forming.

While the pressure sensing unit 14 is represented as comprising a single sensor 30 containing three transducers 40 that define a triangular pattern, it is within the scope of the invention for any one or more of the sensing units 14 of the system 10 to comprise any number of sensors 30 and/or transducers 40, which may promote the reliability and accuracy of the system 10. As nonlimiting examples, two or more transducers 40 may be used to define a linear pattern, three or more transducers 40 may be used to define a triangular pattern, etc. Preferably, the sensor 30 may also comprise a vibration device for alerting the patient to the sensor 30 causing an alarm and encouraging the patient to move in such a way as to relieve pressure from that sensor 30. Finally, it should be noted that the components of the sensing units 14 may be constructed to be sufficiently thin to reduce pressure on and provide greater comfort for the patient. Such components may include multi-layer thin film sensors, thin-film PCBs, thin-film batteries, etc.

In view of the foregoing, it should be apparent that the construction of the sensor 30 and transducers 40 largely determines the sensitivity and pressure threshold of the pressure sensing units 14. Though various configurations are possible, in practice suitable results have been obtained with the RK series of dome sensors commercially available from Snaptron, Inc. A particularly suitable dome sensor is believed to be part number RK50040, which is reported to have a maximum trip force (Fmax) of about 40 grams. In investigations leading to this invention, a 40 gram trip force applied to the RK50040 dome has been correlated to a minimum pressure level of about 32.5 mmHg (about 4330 Pa).

The construction of the sensing units 14 preferably allows each sensing unit 14 to be applied and secured to a patient's body, such as to one or more bony prominences that are susceptible to damage from soft tissue pressure. The sensing unit 14 may be located within a disposable sleeve that can be slipped over the carrier 32 to allow reuse of the sensing unit 14.

The converter 12 preferably contains circuitry (not shown) capable of wirelessly monitoring electrical outputs generated by each pressure sensing unit 14 over whatever time period has been selected by a caregiver. The converter 12 also preferably contains circuitry (not shown) adapted to record locations, identifications, and pressure data of the sensors 30 of the pressure sensing units 14. For example, the converter 12 may be configured to accept Bluetooth® low energy (BTLE) data streams from the pressure sensing units 14. The converter 12 also preferably contains circuitry (not shown) adapted to wirelessly connect to the tablet 13 in order to transfer data collected by the converter 12 from the pressure sensing units 14. For example, the converter 12 may send a WiFi® signal to the tablet 13 to download a single stream of data into the application software residing on the tablet 13.

The converter 12 is preferably configured to receive BTLE signals from the sensors 30, preferably at least up to six sensor signals, and convert these BTLE signals into a single WiFi® signal that includes at least the identity of each sensor and the data corresponding to each sensor. The converter 12 transmits the WiFi® signal to the tablet 13 and the software application on the tablet 13 processes the WiFi® signal, identifies each sensor 30 and its corresponding data, analyzes and provides the data to the caregiver via the display 26 and GUI. The tablet 13 may further transmit the analyzed data to other devices, such as a nurses' station, a mobile device, or a remote database.

Figure 3:
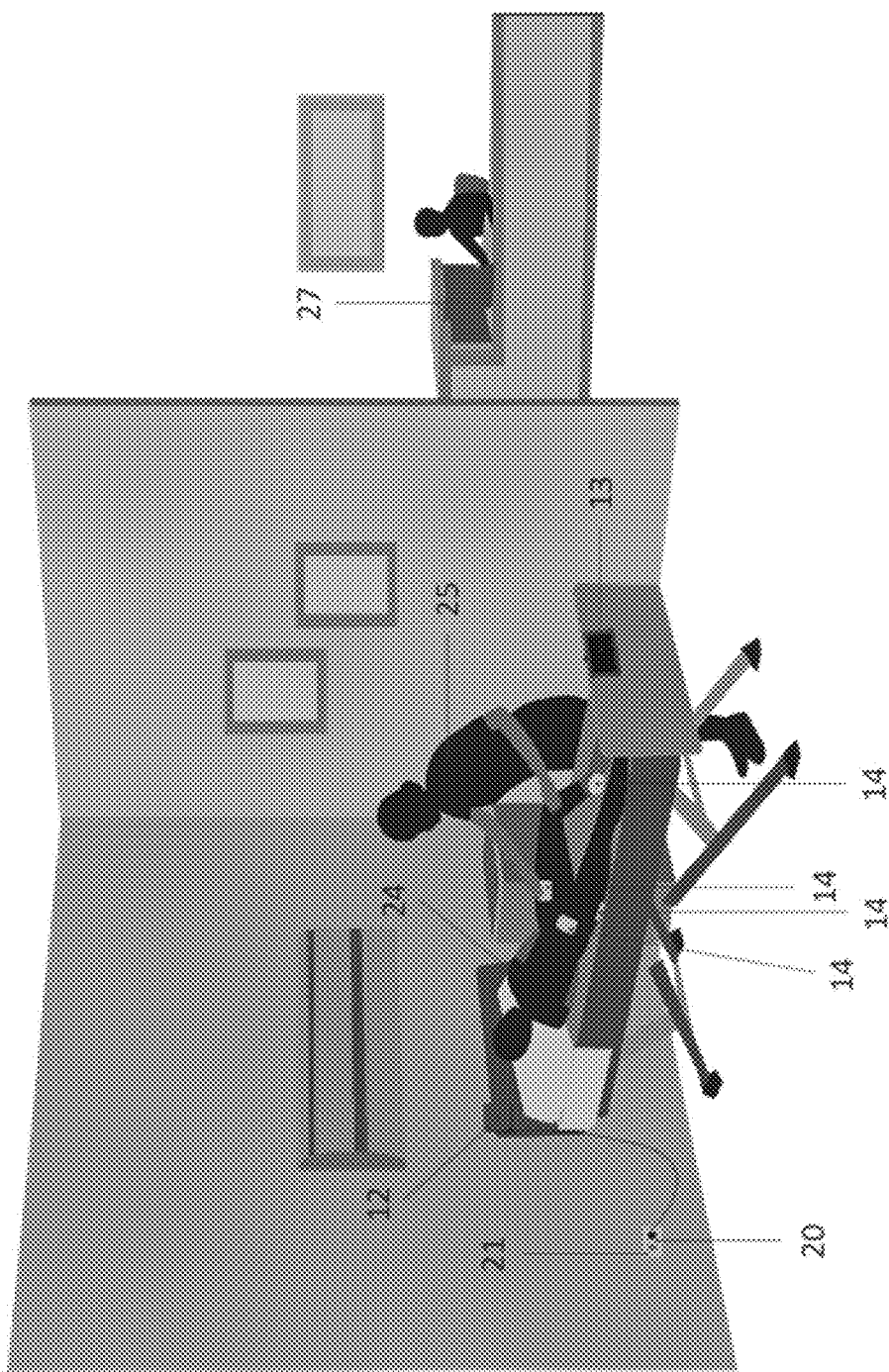
FIG. 3 represents a setting in which a patient may be wirelessly monitored with the pressure monitoring system of FIG. 1.

A nonlimiting method of using the system 10 is represented in FIG. 3. As represented, the converter 12 may be located near a patient 24 with its power converter 20 plugged into an outlet 21. The pressure sensing units 14 are shown as located over one or more anatomic sites on the patient 24 by a caregiver 25. The tablet 13 may be located in any position within range of the wireless connection to the converter 12.

The caregiver 25 may use the touchscreen capability of the display 26 of the tablet 13 and its GUI to guide the caregiver 25 during an information input phase of the setup for the system 10, for example, to input an identification of the patient 24, input clinical data and site locations of the pressure sensing units 14, and select a time threshold designating the amount of time in which the number and duration of pressure excursions may be above a threshold pressure level during an assessment prior to an alarm.

Figure 4A:
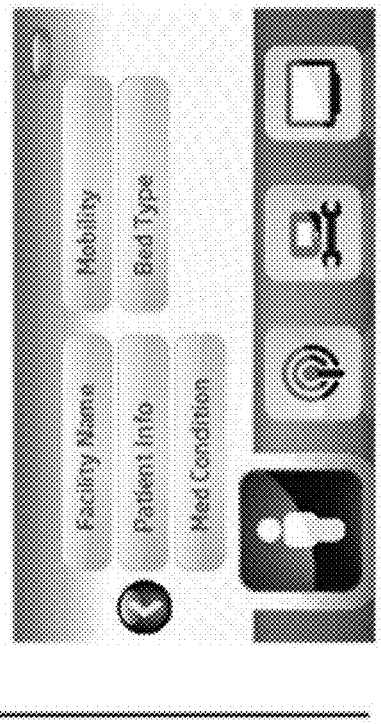
FIGS. 4A and 4B represent graphic user interfaces providing for the input of patient information and alarm time, respectively, in accordance with a nonlimiting aspect of this invention.
Figure 4B:
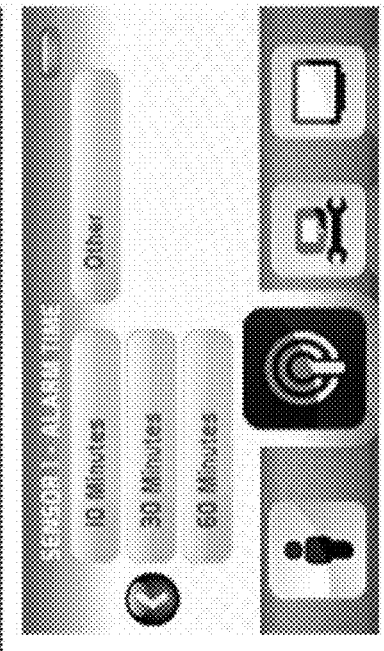
Figure 5A:
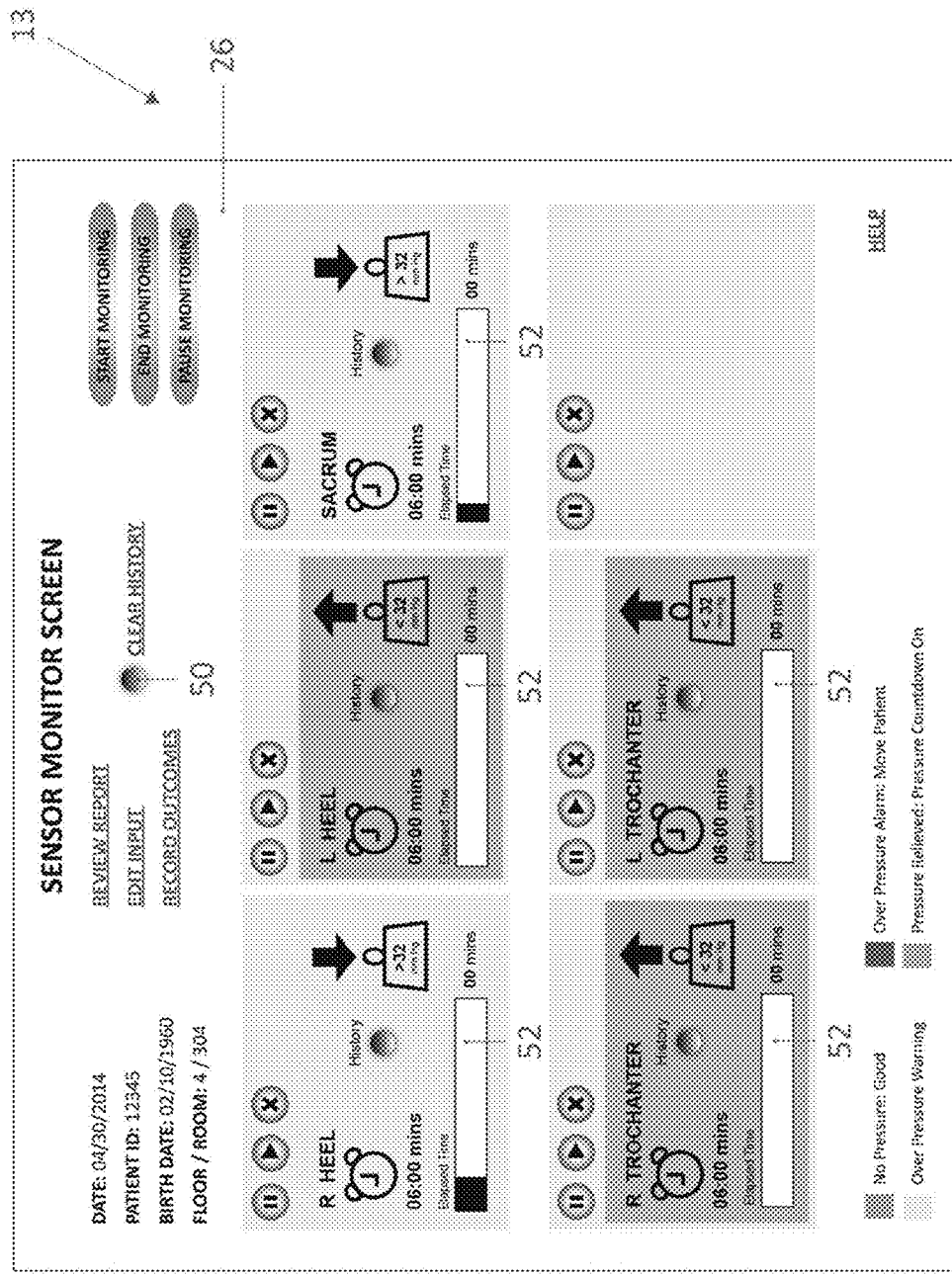
FIGS. 5A and 5B represent a graphic user interface displaying a status of activated pressure sensing assemblies in accordance with a nonlimiting aspect of this invention.

FIGS. 4A and 4B are representative of an exemplary graphical user interface for the information input phase of the system 10. Each pressure sensing unit 14 is preferably identified in the application software as to its individual anatomic placement. Each of the sensing units 14 may also be physically marked on a backside of the sensing unit 14 by the caregiver 25 as to its anatomic placement. As represented in FIG. 5A, individual monitor screens on the tablet 13 may show each of the locations of the sensing units 14 so the caregiver 25 will know which location will have caused an alarm. The patient 24 may also see or hear the alarm, but preferably will also feel vibration if the sensor 30 of a pressure sensing unit 14 is equipped with a vibration device.

During an initial hardware setup phase, the tablet 13 may wirelessly send patient data, for example, by WiFi®, to the converter 12. The converter 12 may then record the locations and identifications of the pressure sensing units 14. As indicated in FIG. 1, the converter 12 may include LED lights 16 corresponding to each sensing unit 14 that indicate when the monitoring function of each sensing unit 14 begins (for example, three connected sensing units 14 equal three green LEDs). The LED lights 16 may also indicate if one or more of the sensing units 14 has malfunctioned, for example, due to battery life. Preferably, the converter 12 has at least two days of stored battery life and an additional LED light 18 to warn of battery failure of the converter 12.

During operation, the pressure sensing units 14 individually sense a load applied thereto and send wireless signals to the converter 12, which then communicates the data to the tablet 13. In FIG. 5A, the software application of the tablet 13 is in communication with the converter 12 and receives a cumulative output signal generated by the converter 12 of the counter based on the electrical outputs of each individual pressure sensing unit 14 over the preselected time period. As previously described, the output value of the counter is cumulative in that it takes into consideration whether the soft tissue pressure has exceeded the preselected pressure level established by the transducers 40 of the sensor 30 during the preselected time period, as well as whether the soft tissue pressure has dropped below the predetermined pressure level during the time period. In this example, the converter 12 is wirelessly in communication with five pressure sensing units 14. The sensors 30 of three of the units 14 are not sensing a load that exceeds a threshold of, for example, 32 mmHg, as indicated by an upwards pointing arrows and their respective empty elapsed time progress bars 52. The sensors 30 of the remaining two units 14 are represented as having sensed a load, as indicated by downwards pointing arrows and partially-filled elapsed time progress bars 52. In addition, these two sensing units 14 are distinguished by having different colored monitor windows as compared to the three sensing units 14 that are not sensing a load. As explained previously, if the patient 24 were to change position and thereby load or unload individual sensors 30, the monitor screens would be updated accordingly. In the case of removing the load from one the pressure sensing units 14, the partially-filled elapsed time progress bar 52 would begin to recede over time according to the conditions set by the caregiver 25 during the information input phase, with the rate of recession corresponding to a decrease in the counter value that occurs at a predetermined ratio relative to the actual elapsed time that the load has not been sensed or otherwise has not exceeded the preselected pressure threshold.

Figure 5B:
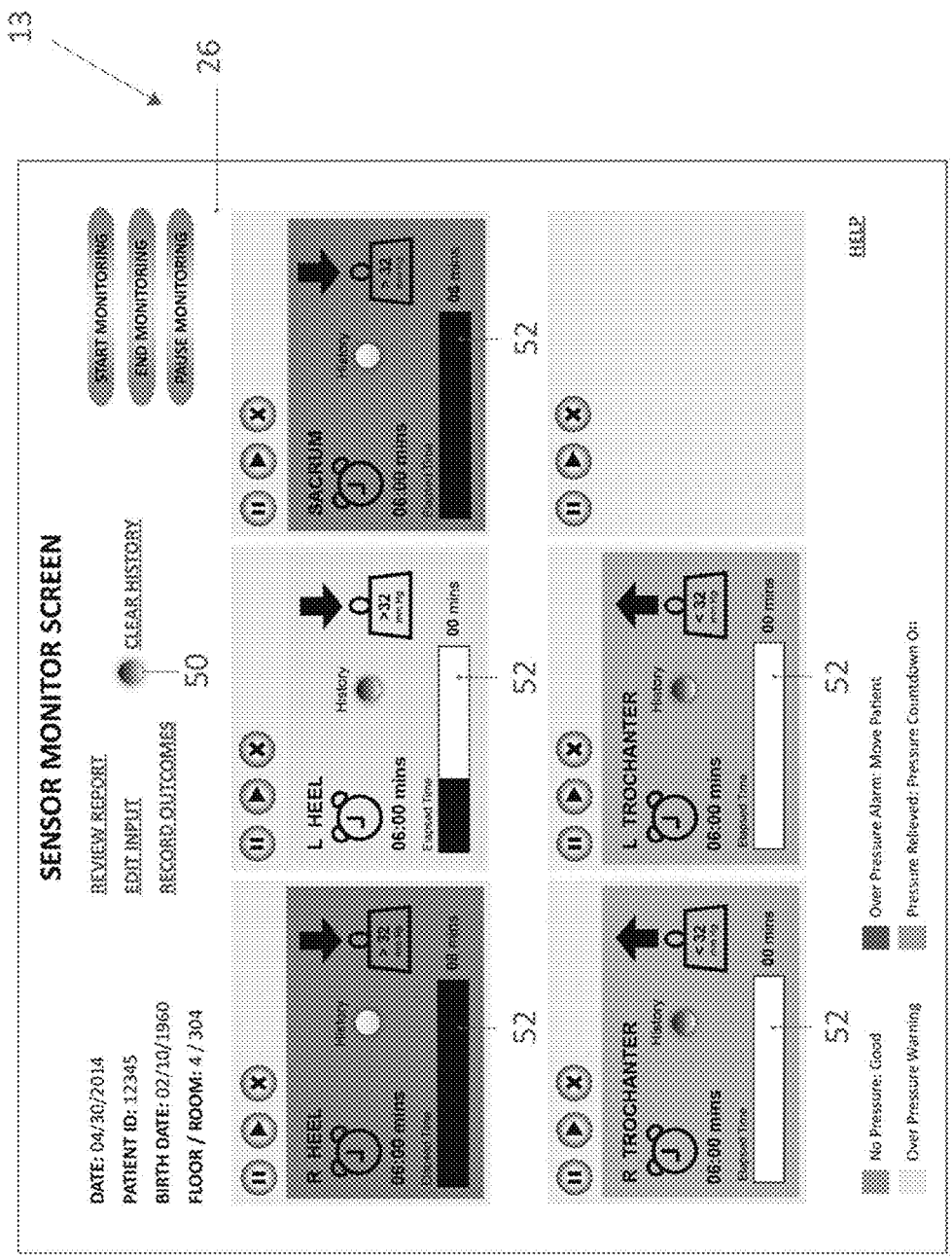

When the pressure level sensed by any one of the pressure sensing units 14 has exceeded the preselected pressure threshold for a time period that exceeded the preselected time threshold, as represented by the completely filled progress bars 52 for two of the sensing units 14 in FIG. 5B, the corresponding monitor screen may activate an alarm. As an example, the monitor screen may flash a red visual alarm (as represented by the darker windows in FIG. 5B) and/or an audio alarm on the tablet 13 to warn the patient 24 and caregiver 25. In addition, the vibration device in the individual sensing unit 14 which surpassed its time threshold may also be activated to directly notify the patient 24 what area of their body to move. In the event of an alarm being activated, wireless signals may be sent to other devices or displays, for example, wall monitor screens, nursing station personal computer screens (such as computer 27 in FIG. 3), mobile phones, etc., in order to alert others to the situation.

The warnings generated by the tablet 13 and any one or more individual pressure sensing units 14 preferably continue until the soft tissue pressure sensed by the sensing unit 14 drops below the predetermined pressure level. At this time, the monitor screen elapsed time bar 52 may start receding over time, corresponding to a decrease in the counter value at the predetermined ratio. Preferably, the application software further displays a history light 50 or similar indicator on the tablet 13, and is used as an indication of the accumulated alarm time on the counter. In a currently preferred embodiment of the invention, when the pressure sensed by a sensing unit 14 drops below the pressure threshold as a result of the patient being moved off the monitored pressure ulcer, the audio and visual alarms on the tablet 13 associated with that sensing unit 14 turn off. However, the history light 50 on the tablet 13 preferably remains lit to indicate to the caregiver 25 that an alarm has previously been activated, even if the alarm is no longer active. Preferably, the history light 50 remains lit until deactivated by the caregiver 25.

Figure 6:
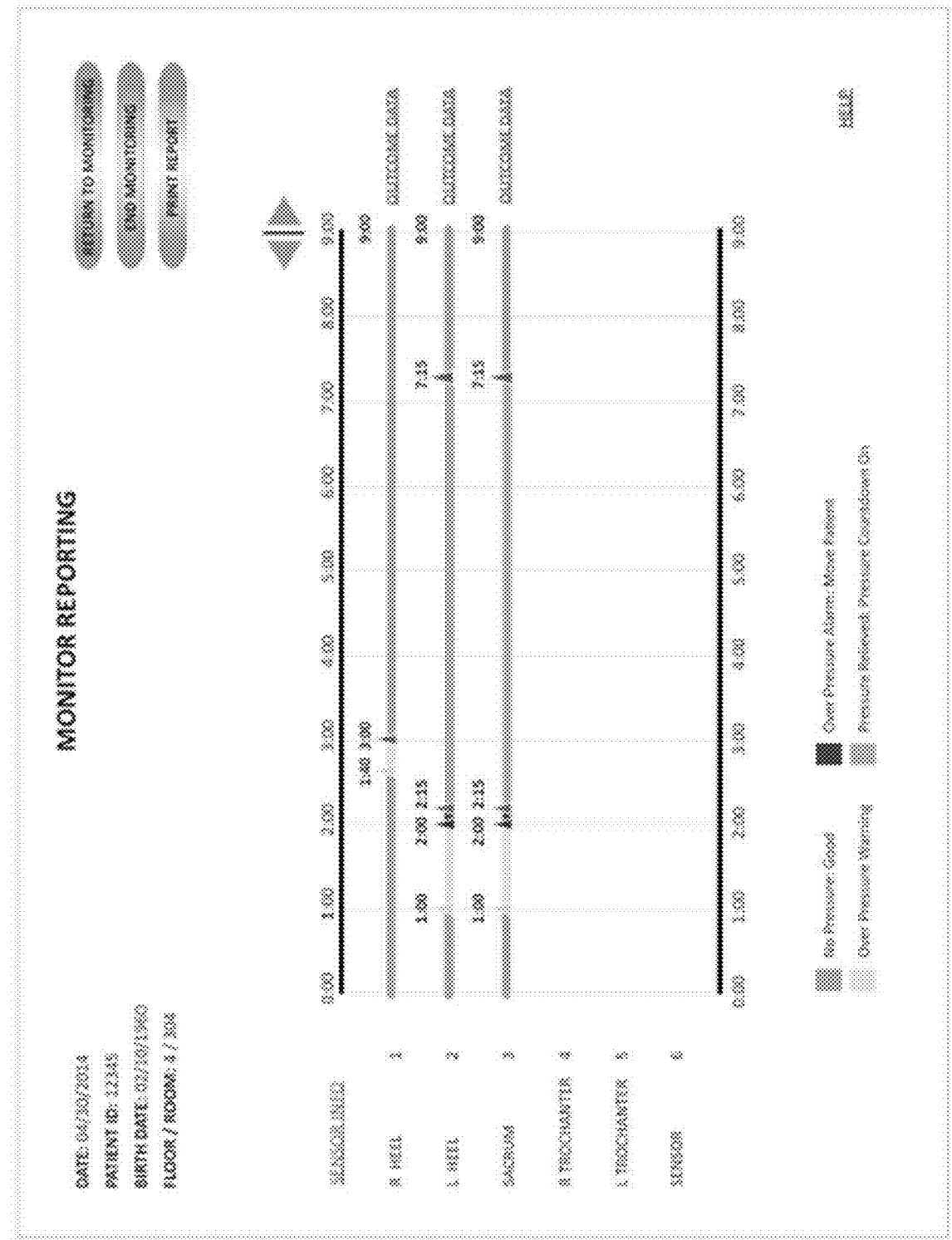
FIG. 6 represents a report displaying historical data pertaining to a patient based on a recording taken while the patient was wirelessly monitored with the pressure monitoring system of FIG. 1.
Figure 8:
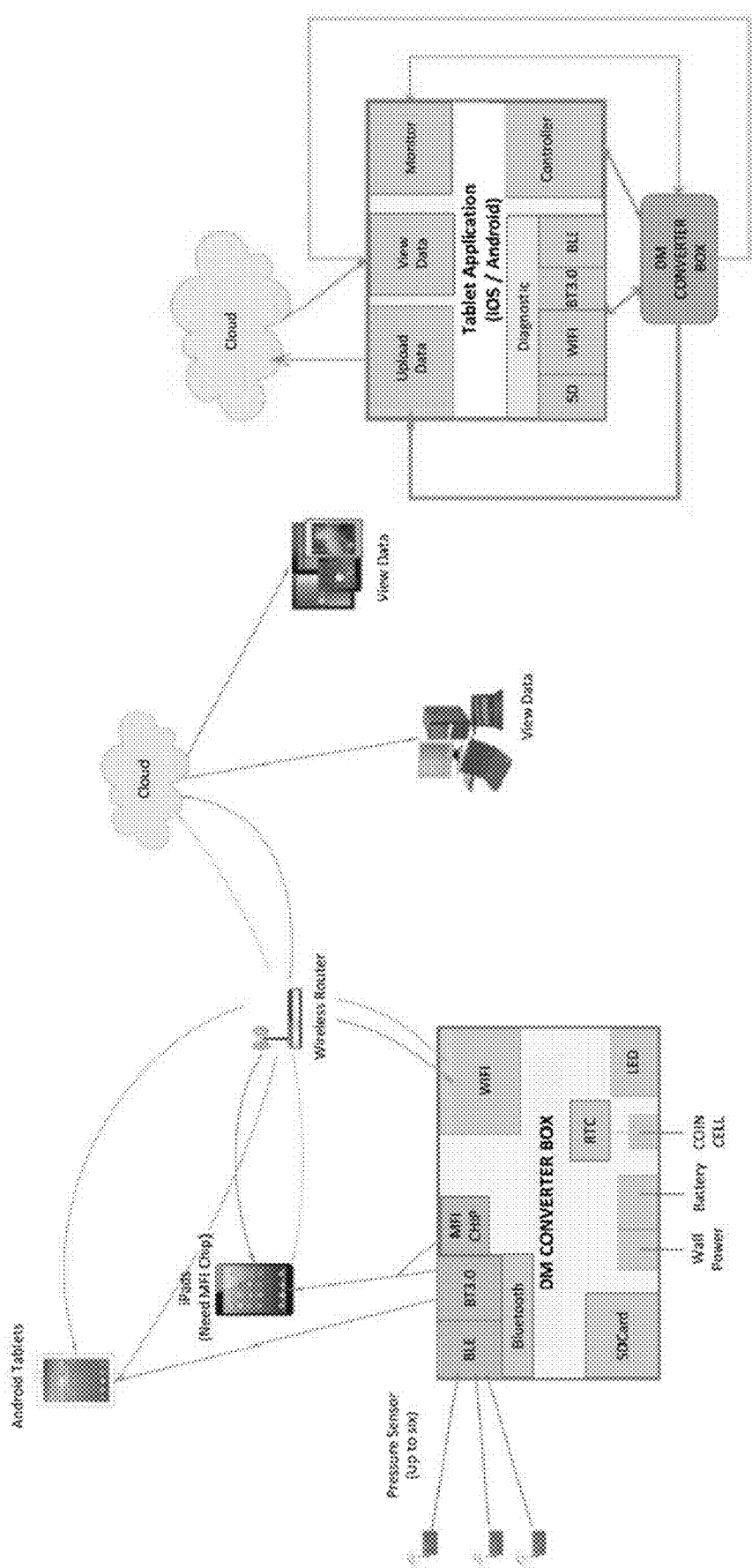
FIG. 8 represents wireless communications between the pressure monitoring system of FIG. 1 and remote devices.

The tablet 13 preferably records all monitoring activities by wirelessly communicating with a facility storage system and/or private or public cloud-based storage systems. FIG. 6 represents an exemplary report format that may be accessible to the caregiver 25 or others both to provide improved care to the patient 24 and to provide historical data for industry or research. As represented, the recorded historical data may include the status of each individual sensing unit 14 over a predetermined period of time. FIG. 8 represents wireless communications between the pressure monitoring system of FIG. 1 and remote devices, such as tablets, databases, and a cloud-based storage systems. As represented in FIG. 8 (top left), the sensors 30 of the sensing units 14 may send signals to the converter 12, which then communicates with a tablet 13 (two different types shown), which then may communicate further through a standard network system with remote devices such as computers, mobile phones, and databases. In addition, FIG. 8 (bottom right) represents internal details regarding the tablet 13 relating to its communication with the converter 12 and remote devices.

When the monitoring process has stopped, ended, or been paused, the application software may require the caregiver 25 to complete an outcome report or survey. The outcome report may show the final status of the patient 24 and the wound or risk skin area at the time when the sensing units 14 are removed from the patient 24 and the monitoring process has ended. The outcome report may be recorded in the facility storage system, and/or private or public cloud-based server for review or research purposes tied to a unique identification tag but may no longer be attached to a particular patient. According to a preferred aspect of the invention, the report format (FIG. 6) may include a link or virtual button for providing access to the outcome report. FIG. 9 represents an exemplary outcome entry format that may be accessible to the caregiver 25 or others both to provide ulcer status reporting for each anatomic area and includes pressure ulcer grade.

Figure 10:
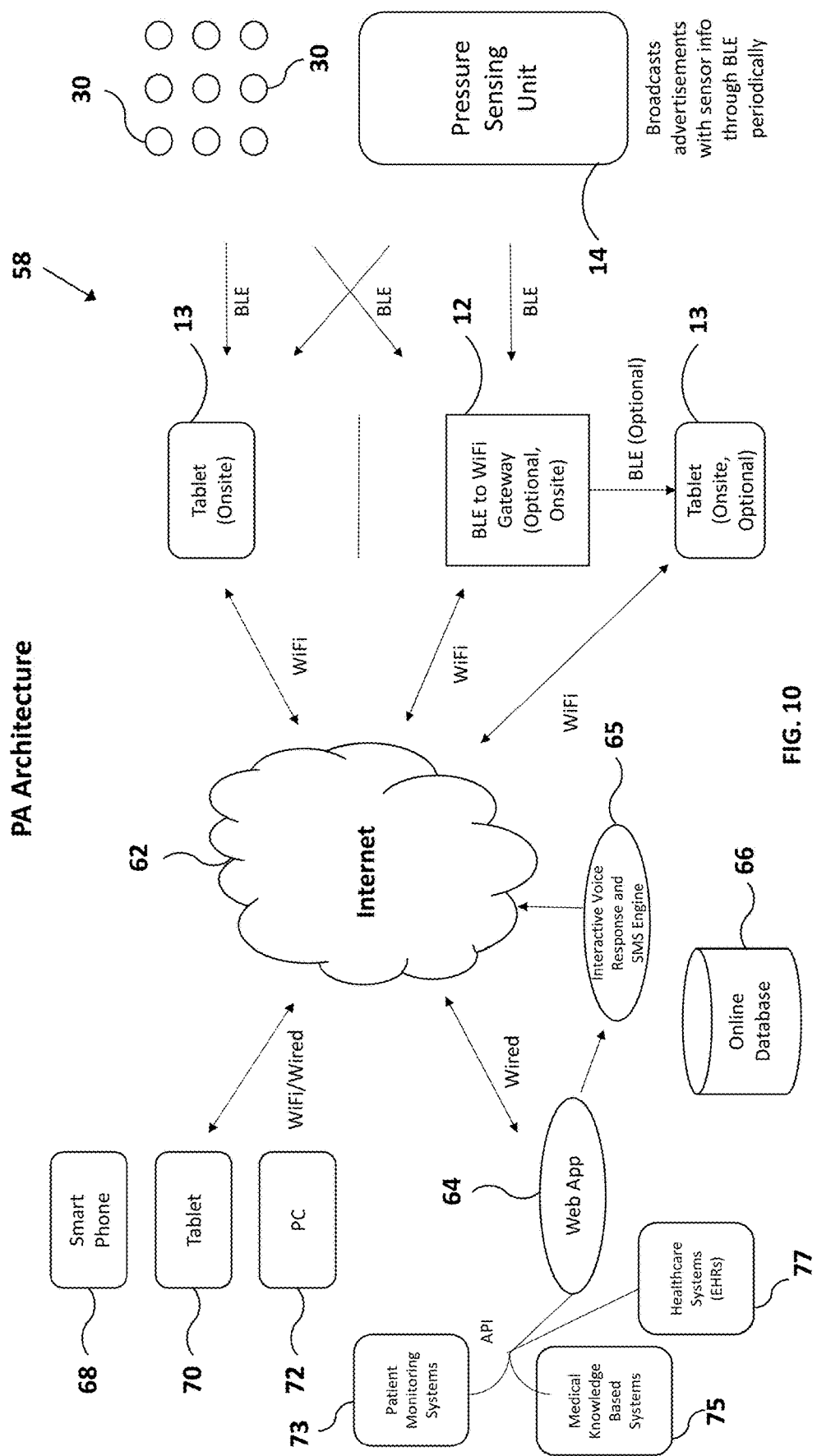
FIG. 10 represents an architectural schematic representation of a pressure monitoring system in accordance with another embodiment of this invention.

FIG. 10 is an architectural schematic representation of an alternative pressure monitoring system 58. For convenience, identical reference numerals are used in FIG. 10 to denote elements that are the same or functionally correspond in at least some aspects to elements described for the system 10 of FIG. 1. The system 58 is shown as including multiple individual sensors 30 that may comprise one or more pressure transducers 40 (not shown), a pressure sensing unit 14 in which multiple sensors 30 may be embedded, an onsite tablet 13, an optional onsite converter or gateway 12, an Internet cloud 62, a web application 64 communicating with an interactive voice response (IVR) and Short Message Service (SMS) engine 65 that is connected to the cloud 62, an online database 66, an optional smartphone 68, an optional offsite tablet 70, and an optional offsite personal computer 72. The engine 65 is preferably configured to verbally communicate with users and patients, particularly so that the latter maybe made aware of which sensor 30 is associated with a warning so that, if possible, the patient may then be able to take corrective action without the involvement or intervention of a caregiver. The web application 64 also communicates through Application Program Interfaces (APIs) with a patient monitoring system 73 and a medical knowledge-based system 75, which are shown as being directly accessed through the web application 64 but could be web-based and accessed via the Internet cloud 62. The sensing unit 14 with multiple embedded sensors 30 broadcasts sensor data periodically through BTLE signals to the optional gateway 12 (if present) and/or the onsite tablet 13. Similarly, the sensing unit 14 also periodically broadcasts BTLE signals representing the sensor data to the optional gateway 12 (if present) and/or the onsite tablet 13. The optional gateway 12 may also broadcast BTLE signals directly to the onsite tablet 13.

The Internet cloud 62 is wirelessly connected to at least one of the onsite tablets 13 and the optional gateway 12 for two-way wireless communication between these devices and the cloud 62. The web application 64 and the online database 66 are both in two-way communication with the cloud 62, for example, through a wired connection. Finally, the smart phone 68, the offsite tablet 70, and the offsite PC 72 are also in two-way communication with the cloud 62 using any combination of wireless or wired signals.

Figure 11:
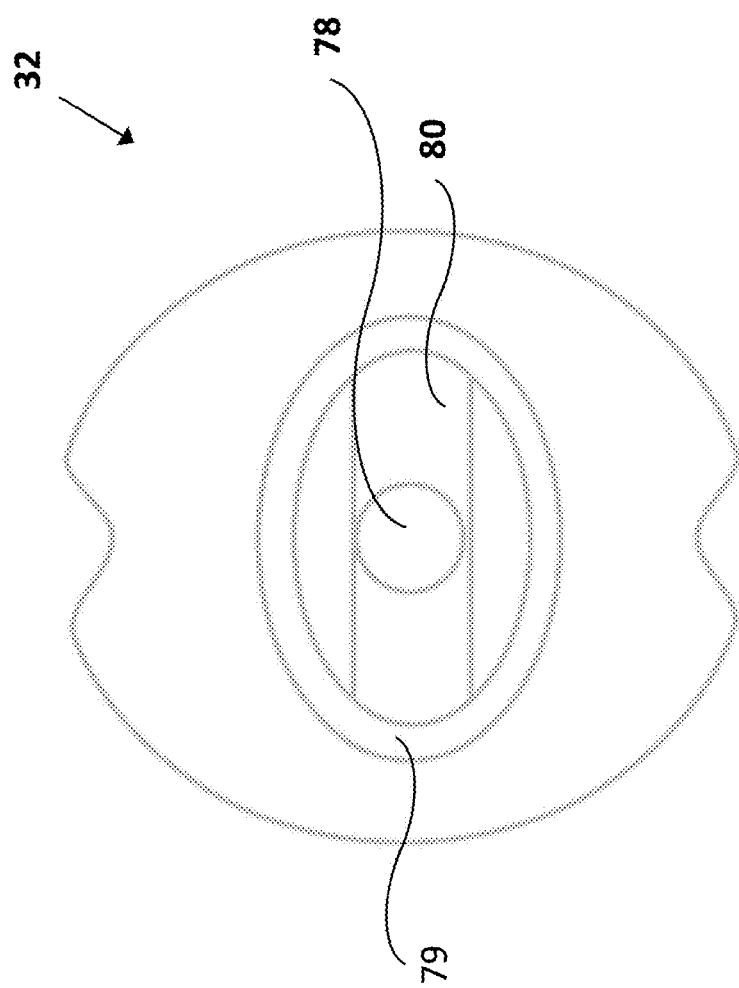
FIG. 11 represents a carrier for another embodiment of a pressure sensing unit suitable for use with the systems of FIGS. 1 and 10.
Figure 12:
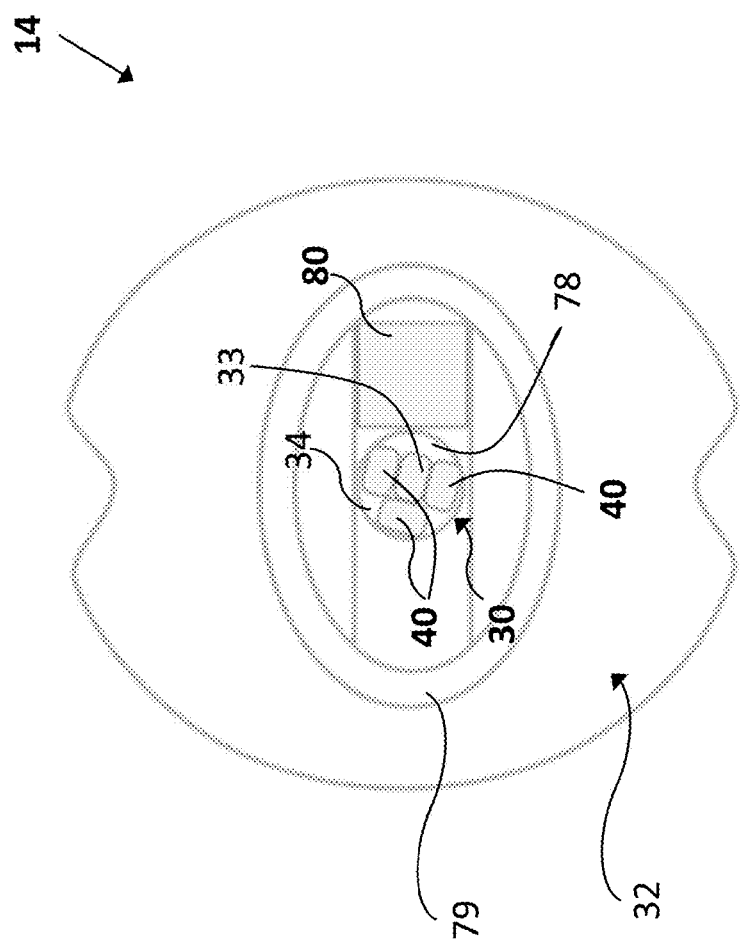
FIG. 12 represents a pressure sensing unit comprising sensors assembled with the carrier of FIG. 11.
Figure 13:
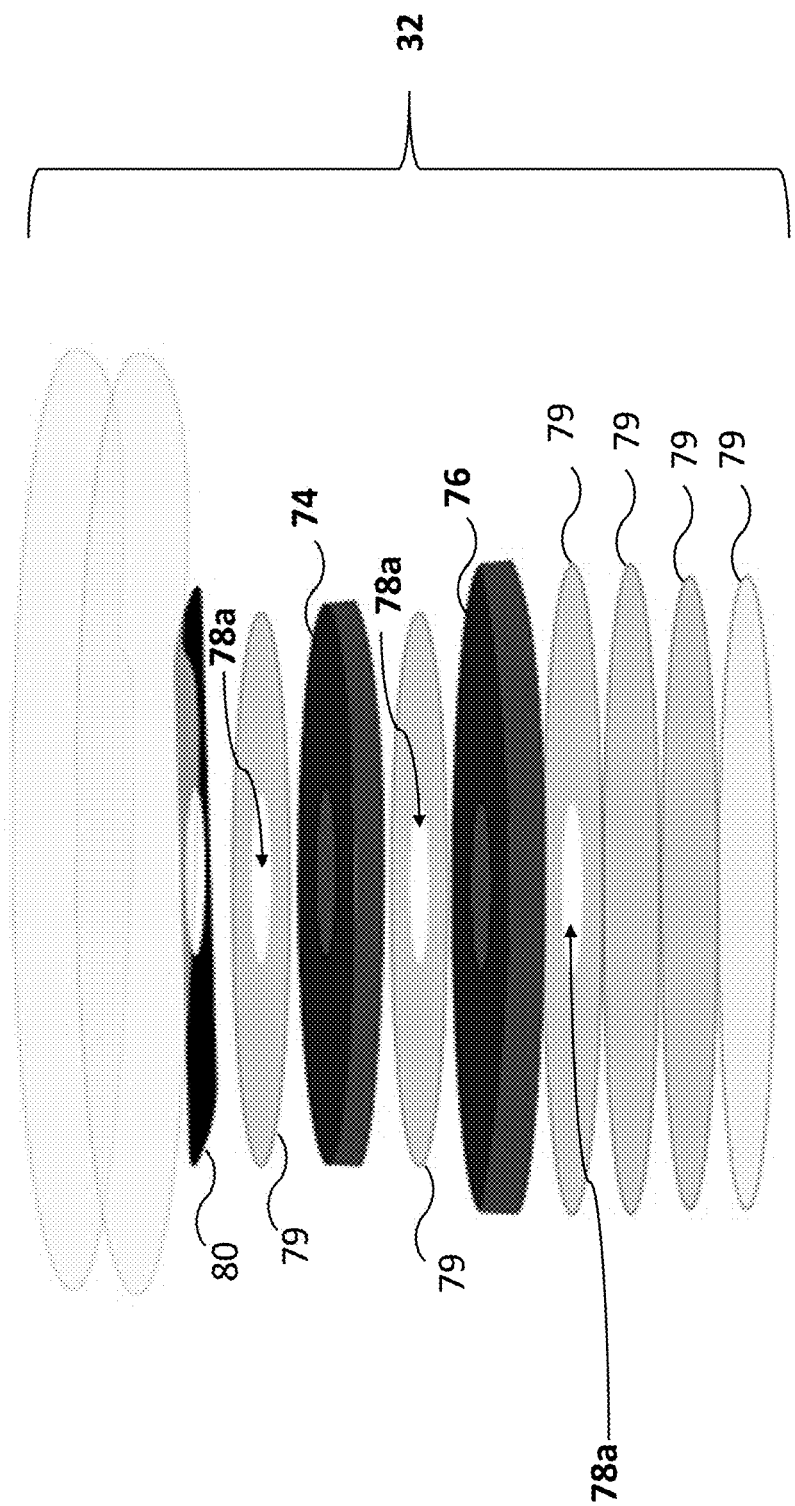
FIG. 13 represents an exploded view of the carrier of FIG. 11.

FIGS. 11-13 represent a particular embodiment of the pressure sensing unit 14. As represented in FIGS. 11 and 12, the sensing unit 14 of FIGS. 11-13 has a round periphery, a central aperture 78 sized to accommodate a sensor 30 (e.g., one or more transducers 40 and a vibration device 33 mounted on a PCB 34), and an adhesive strip 80 that releasably overlies the aperture 78, can be peeled back to allow placement of the sensor 30 in the aperture 78, and then be reapplied over the aperture 78 to secure the sensor 30 within the aperture 78. The sensing unit 14 is preferably sized and shaped for the particular anatomic location on the patient where the sensing unit 14 will be located. As such, alternative shapes may be used and preferred for the sensing unit 14.

As seen in FIG. 13, the sensing unit 14 may be constructed to comprise first and second foam layers 74 and 76 embedded between layers of additional dressing materials 79, which may be formed of a foam, hydrocolloid, alginate self-adherent dressing or other suitable materials. The aperture 78 seen in FIGS. 11 and 12 can be seen in FIG. 13 as being defined by a series of apertures 78a formed within certain layers of the sensing unit 14 that are sized to accommodate the sensor 30, including its transducers 40 and PCB 34. The apertures 78a are formed in the foam layers 74 and 76 and at least the outermost layer of dressing material 79 and the layer of dressing material 79 between the foam layers 74 and 76. The apertures 78a may also be defined in the innermost layers of dressing material 79 so that the sensor 30 can be placed in closer proximity to the patient's skin. In the case of open wounds, the apertures 78a are preferably not present in the innermost layers of dressing materials 79 so that dressing material is present between the sensor 30 and open wound. The lowermost layer of the dressing material 79 directly facing the patient's skin is preferably a non-adhesive foam or absorbent material without an aperture 78a formed therein. In addition, the skin-side surface of the lowermost layer of dressing material 79 directly facing the patient's skin may include an adhesive covering along a narrow border thereof to adhere the sensing unit 14 to the skin.

The systems 10 and 58 are not limited to the use of pressure sensing units 14 of the types shown in FIGS. 2 and 11-13. In particular, the systems 10 and 58 may include handheld probes integrating multiple sensing and data analysis capabilities relying on a variety of sensors including thermal, RBG, 3D, chemical, hyper spectral, and situational awareness sensors.

Figure 14:
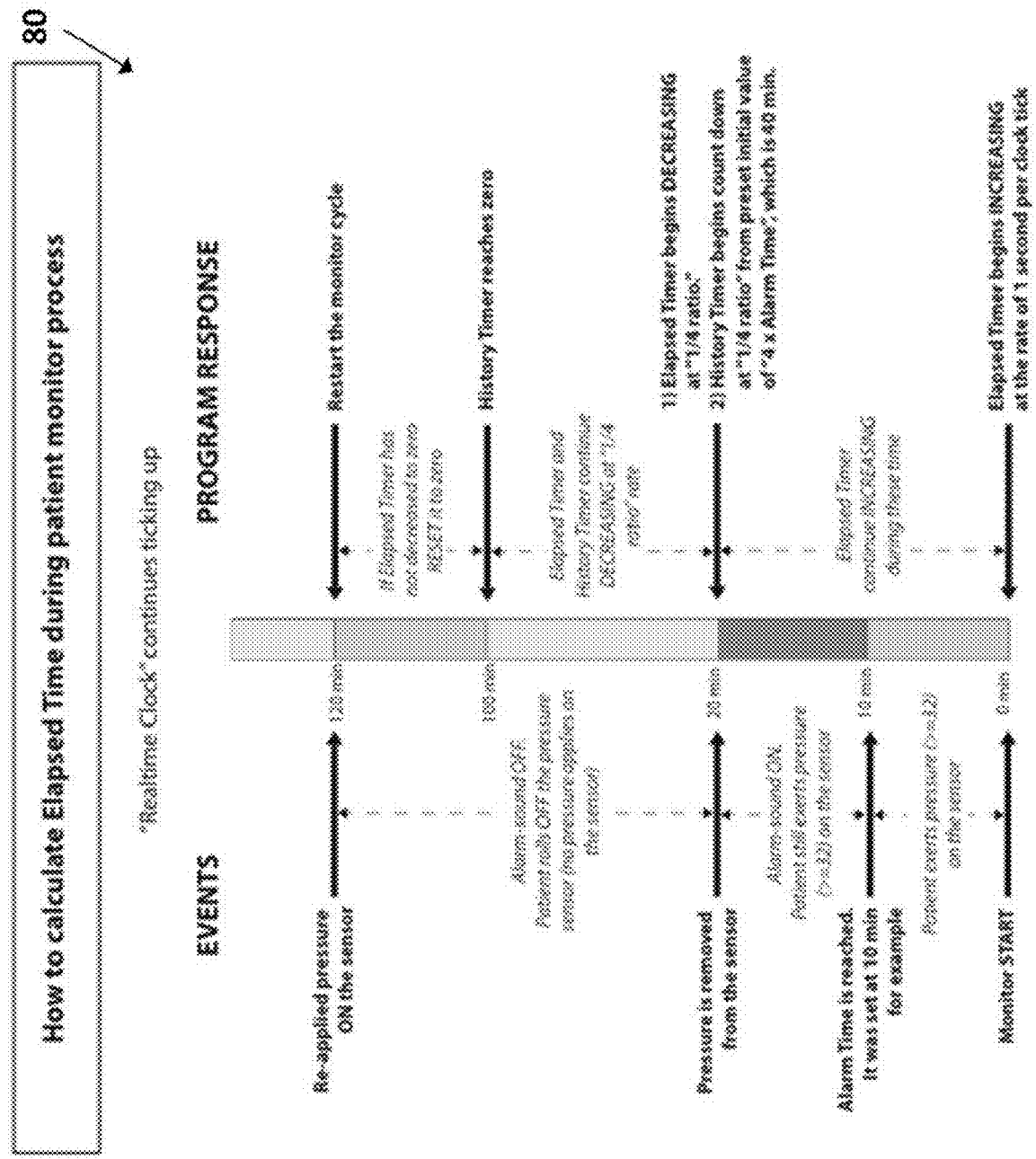
FIG. 14 graphically represents a nonlimiting example of a method for correlating pressure and time to provide alarms during patient monitoring processes that can be performed with the systems of FIGS. 1 and 10.

FIG. 14 schematically represents an example of the activity of a counter during a patient monitoring process including a series of events that correspond with a series of program responses. As with the system 10 of FIG. 1, the system 58 of FIG. 10 preferably utilizes a separate counter associated with each pressure sensing unit 14, and whose value increases once the soft tissue pressure detected by the associated pressure sensing unit 14 exceeds a predetermined pressure threshold, but decreases while the soft tissue pressure is below the threshold. In addition, the counter value may increase and decrease at different rates, for example, increase at a ratio relative to actual elapsed time (e.g., a ratio of 1:1 relative to actual elapsed time) that is higher than the ratio at which the counter decreases relative to actual elapsed time (e.g., a ratio of less than 1:1 relative to actual elapsed time). The counter value can be calculated by any suitable microcontrol, program, etc., and the increments at which the counter value is calculated can be intervals of minutes, seconds, or fraction thereof. In alternative embodiments of the systems 10 and 58, the rate at which the counter value increases or decreases compared to elapsed time may be modified on the basis of different variables, including but not limited to variable pressure data obtained with the use of a variable output pressure transducers (instead of on-off switch-type transducers), elapsed time during an alarm event, the particular body part causing the alarm condition, alarm history, historical sensor data, and/or data relating to the patient, e.g., patient characteristics such as age, gender, health/medical condition, etc. Yet another alternative is for the counter value to simply reset to zero after a predefined number of minutes of elapsed time at a sensed pressure below the threshold. Such alternatives may be particularly of interest as the understanding of pressure ulcers evolves. Given that pressure ulcers are impacted by the amount of pressure applied over a period of time, the use of variable output pressure transducers may be preferred to implement an algorithm capable of computing a counter decrease ratio that addresses the effects of different levels of pressure over different levels of time, including peak, trough, average, and median pressures in relation to time, the specific part of the body subjected to that pressure, and patient data. For example, if a body region of a patient is subjected to a pressure of 32 mmHg over a period of 60 minutes, 240 minutes (corresponding to a counter decrease ratio of 1:4) may be an adequate duration of time to recover after the pressure has been relieved, whereas the same body region subjected to a pressure of 75 mmHg for 60 minutes may require a longer recovery duration, for example, 300 minutes (corresponding to a counter decrease ratio of 1:5).

As a nonlimiting example, on the basis of a counter increase ratio of 1:1 and a counter decrease ratio of 1:4, calculating the counter value may be as follows:

Current Counter Value=(Initial Counter Value)+
(Time at Pressure Exceeding Pressure Threshold)−(Time at Pressure Below Pressure Threshold)/4

According to this formula, the counter value in FIG. 14 increases from an initial value of zero at a rate of 1:1 relative to actual elapsed time for a period of twenty minutes while the soft tissue pressure sensed by the associated pressure sensing unit 14 exceeds a predetermined pressure level, in this example, a threshold of 32 mmHg. FIG. 14 represents that the system 10/58 has been programmed to include an alarm threshold, whereby an alarm (e.g., audible, vibrational, etc.) is activated once the pressure threshold has been exceeded for ten minutes, i.e., the counter value is ten. When the sensed pressure drops below the threshold at twenty minutes, the counter value is at 20 but begins to decrease at a rate of 1:4 relative to actual elapsed time. In FIG. 14, the pressure sensed by the associated pressure sensing unit 14 remains below the threshold of 32 mmHg for 120 minutes, and after eighty minutes of actual elapsed time below the pressure threshold the counter has decreased by twenty (80/4) to return to a value of zero. The counter value remains at zero until 120 minutes, at which time FIG. 14 indicates that the pressure sensed by the associated pressure sensing unit 14 has again exceeded the threshold and the counter value begins to increase from zero at the 1:1 rate relative to actual elapsed time. As indicated in FIG. 14, the alarm is deactivated (turned off) once pressure is no longer sensed by the sensing unit 14. Alternatively, the alarm may be deactivated when the soft tissue pressure no longer exceeds the threshold. To avoid unnecessary alarms, the system 10/58 may employ an algorithm that re-activates the alarm after a predetermined amount of time after the alarm was deactivated. For example, the predetermined amount of time may be based on the amount of time the soft tissue pressure exceeded the threshold. Alternatively, the algorithm may further take into consideration patient data (age, gender, health/medical condition, etc.), the location of the sensing unit 14 on the patient's body, and the soft tissue pressure (e.g., peak, trough, average, and median, etc.).

The systems 10 and 58 can also determine patient diagnosis and recommend treatment based on certain categories of variables. A doctor, nurse, facility or researcher can use a predefined customized classification system (for example, rated on a scale of 1-10) to specify a patient category for a given patient that is based on patient data such as age, gender, health/medical condition, etc. A Braden scale may also be used initially as an assessment tool for predicting the risk of pressure ulcers based on the total of scores given in categories of sensory perception, moisture, activity, mobility, nutrition, and friction or shear. Over time, the medical knowledge-based system 75 (FIG. 10) will preferably accumulate information regarding specific patient and risk characteristics that can be used to refine the patient category assigned to a patient. In combination, the data obtained with the system 10/58 can be used by an algorithm to assign a diagnosis category (e.g., on a scale of 1 to 10) to a patient based on a predefined customized category that reflects the amount of pressure and the amount of time at one location of the patient's body that has specific location characteristics, which may also be rated on a scale of 1-10.

As an nonlimiting example of the above, X amount of pressure for 60 minutes on the sacrum of a patient may be assigned a 5 rating as a diagnosis category. A treatment category can then be based on the diagnosis category as well as the patient category for the patient. For example, based on the diagnosis category (e.g., the amount of pressure, the amount of time for a specific location) and the patient category, the treatment category may be used to specify how long the patient should not be on the particular part of the body, ranked on a scale of, for example, 1-10. For example, given a patient category 8 that has a sacrum rating of 5, the system 10/58 may immediately prescribe a treatment category of 3 on a scale of 1-10.

FIGS. 15-28 represent preferred embodiments of graphic user interface screens that may be displayed on the tablet's display 26 for use by a caregiver to monitor patients using the systems 10 and 58, and particularly the system 58 depicted in FIG. 10. In particular, BLE signals broadcast from a sensor 30 of a sensing unit 14 to the Internet cloud 62 (FIG. 10) are encrypted to HIPAA standards and include a sensor ID, battery status, pressure switch state, and signal strength along with potential additional data. As an example, data is sent from the sensing unit 14 via a configuration setting every 0.5 to every 5 minutes or every 1 to 5 minutes for preventative locations. In preferred embodiments, data can be achieved but not deleted from the system 10/58. All data changes are synched with the cloud 62 when online. When the system 10/58 is offline, data is stored and synched at the first opportunity that the system 10/58 is back online.

Figure 15:
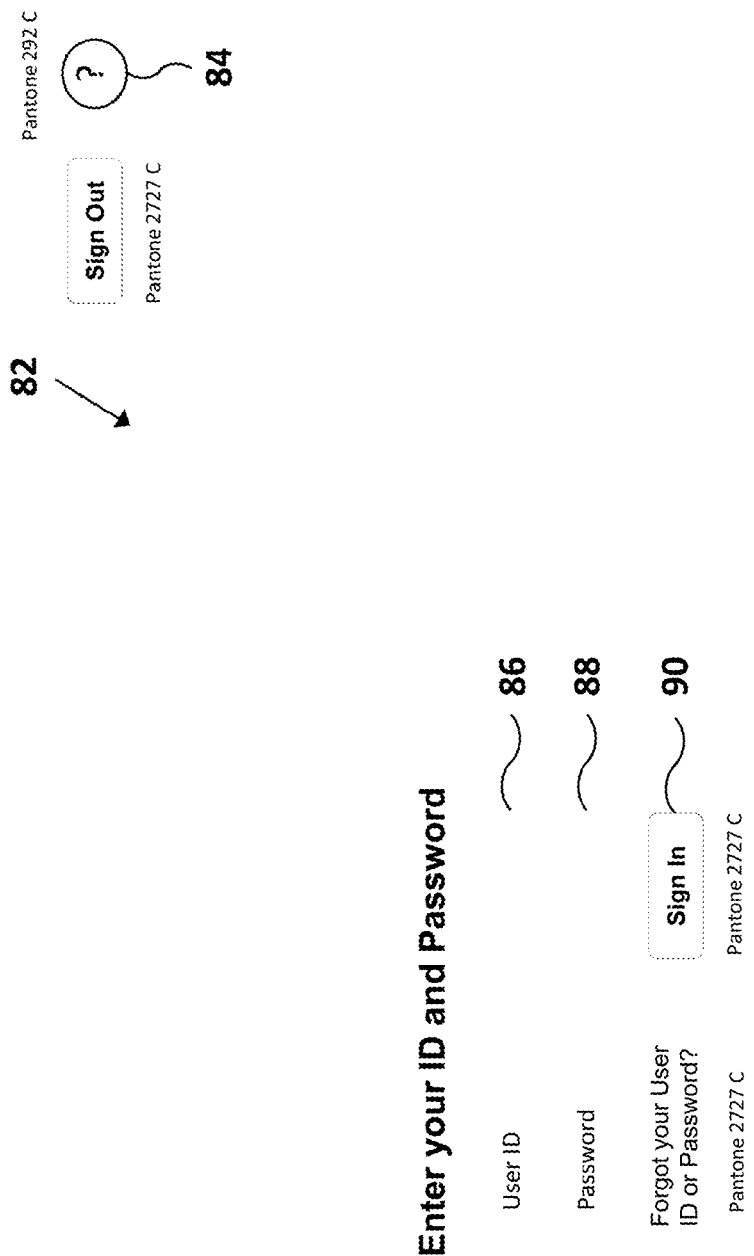
FIG. 15 represents an embodiment of a login page displayed on a graphic user interface suitable for use with the systems of FIGS. 1 and 11.

As illustrated in FIG. 15, after a user directs a browser to the website login page of the system 10/58, a screen 82 appears that includes a question mark icon 84. The question mark icon 84 preferably appears on all interface screens displayed to users of the system 10/58. A user enters a login into a login dialog box 86 and a password into a dialog password box 88, then clicks a sign in dialog button 90 to gain entry into the software.

Figure 16:
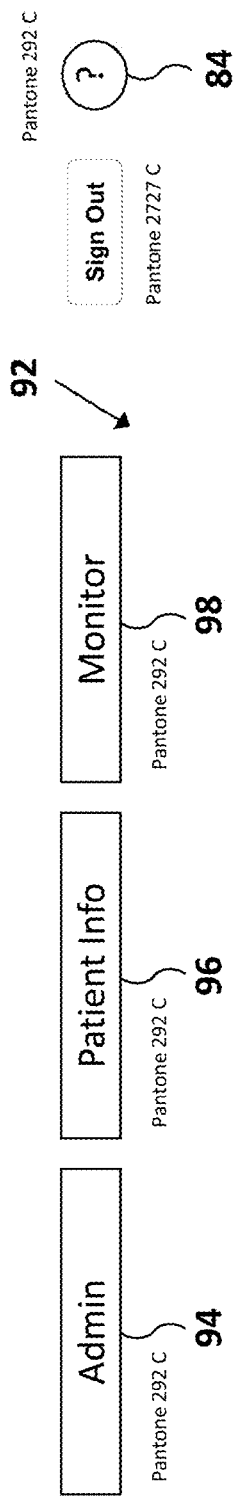
FIG. 16 represents an embodiment of a welcome screen displayed on the graphic user interface of FIG. 15, including administrative, patient information and monitoring tabs.

After a user successfully logs into the system, FIG. 16 illustrates a welcome screen 92 that includes an administration ("Admin") tab 94, a patient information ("Patient Info") tab 96 and a monitor ("Monitor") tab 98. Clicking the administration tab 94 brings the user to an administrative ("Admin") screen illustrated in FIG. 17 that includes additional links including a facilities module 100, a users module 102, a settings module 104, and a reports module 106.

Figure 17:
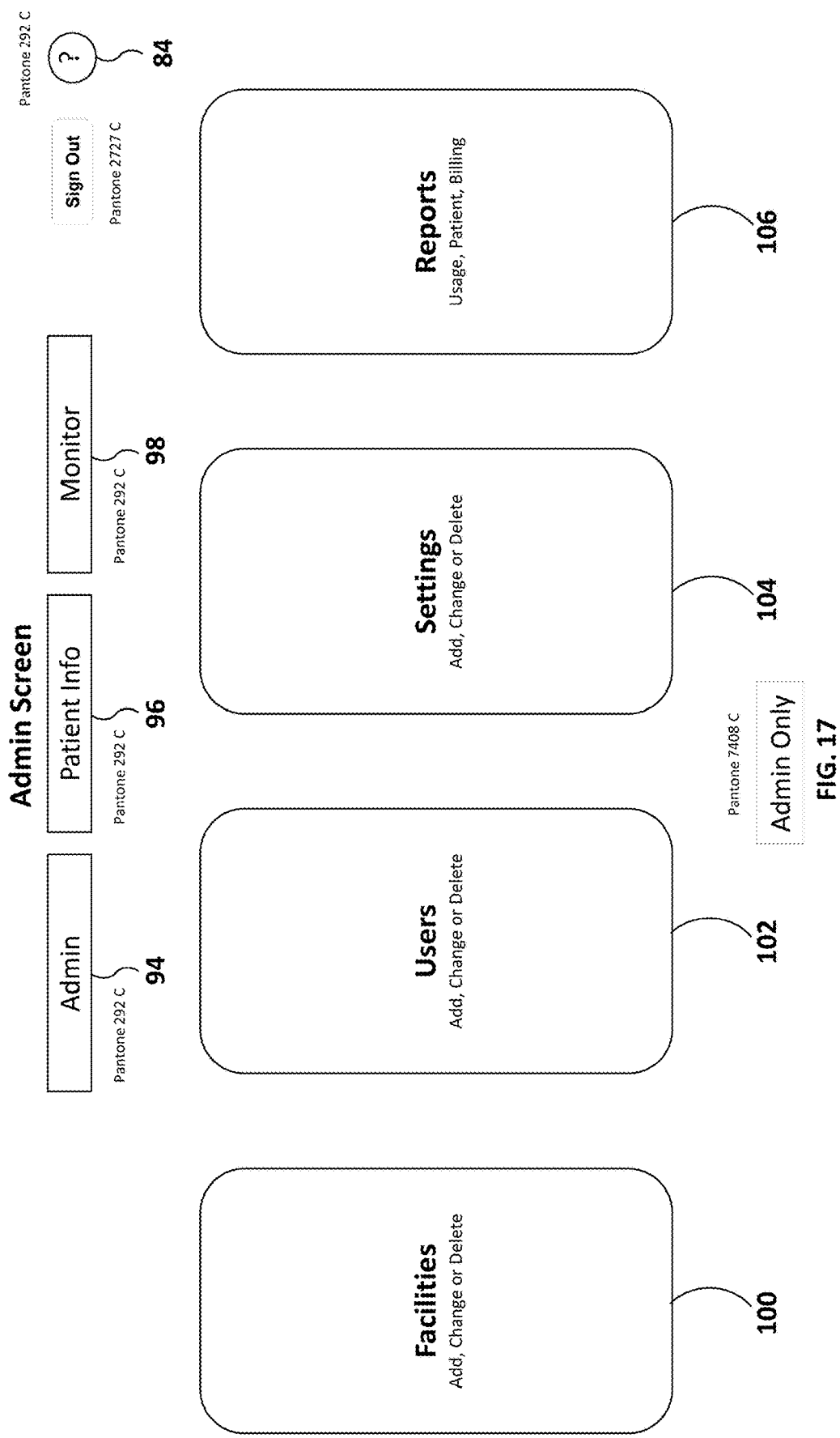
FIG. 17 represents an embodiment of an administrative ("Admin") screen accessed through the administrative tab of the welcome screen of FIG. 16.

FIG. 18 illustrates the facilities module 100 that can be accessed through the administrative screen of FIG. 17 to allow users to add, change and/or delete organizations and sub-organizations, including details such as name, address, floor, and section descriptions. Only certain users such as super users with administrative rights are preferably allowed to add, change, and/or delete certain data in the system 10/58.

Figure 19:
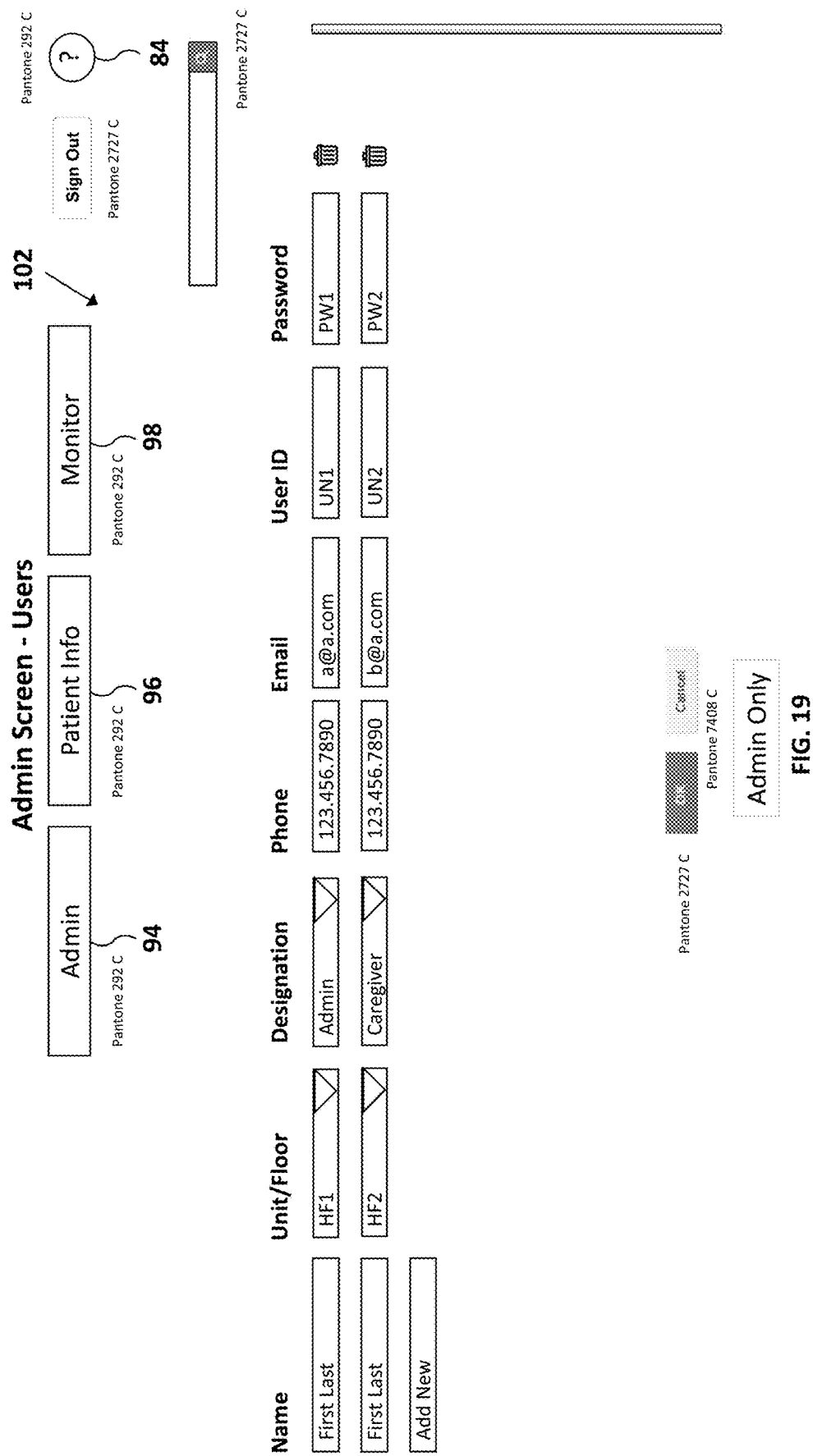
FIG. 19 represents an embodiment of a users module screen accessed through the administrative screen of FIG. 17.

FIG. 19 illustrates the users module 102 that can be accessed through the administrative screen of FIG. 17 to allow users to add, change and/or delete users including details such as name, unit/floor, designation, phone, email, username, and password.

Figure 20:
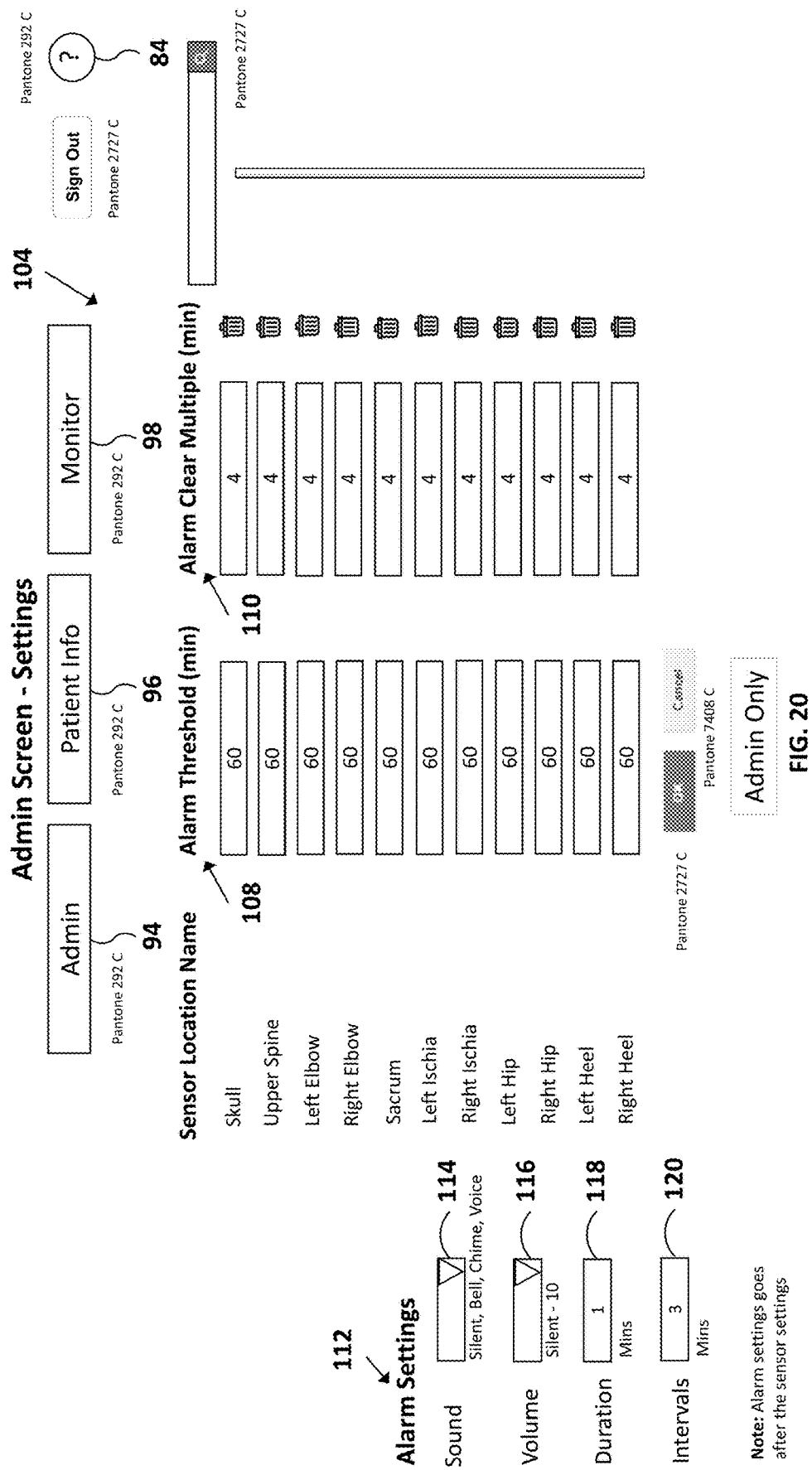
FIG. 20 represents an embodiment of a settings module screen accessed through the administrative screen of FIG. 17.

FIG. 20 illustrates the settings module 104 that can be accessed through the administrative screen of FIG. 17 to allow users to add, change and/or delete certain parameters associated with certain sensors including an alarm threshold 108 (such as that discussed in reference to FIG. 10) and an alarm clear time 110. A set of alarm settings 112 are configurable including a sound option 114, a volume option 116, a duration option 118, and an interval option 120.

Figure 21:
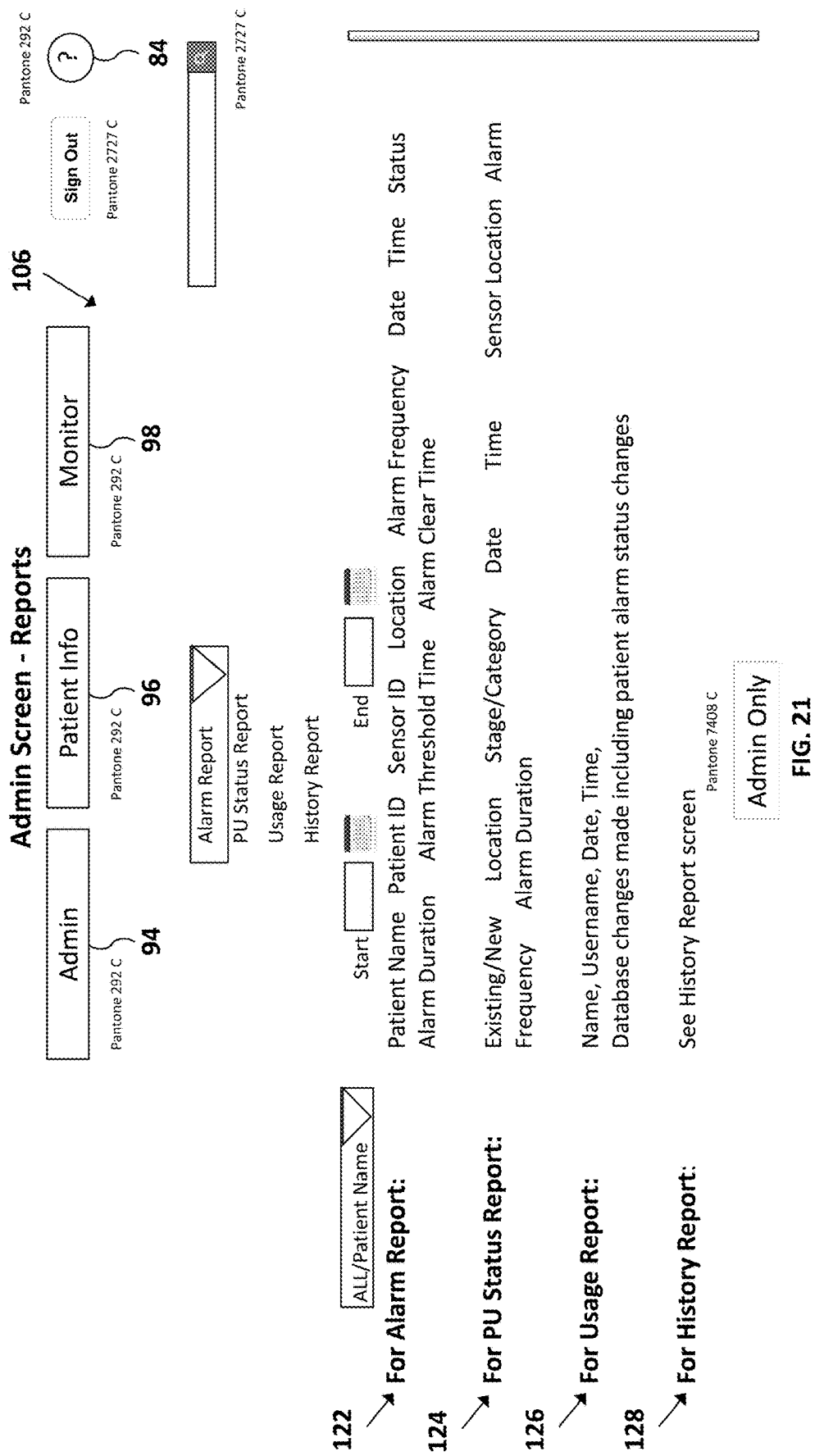
FIG. 21 represents an embodiment of a reports module screen accessed through the administrative screen of FIG. 17.

FIG. 21 illustrates the reports module 106 that can be accessed through the administrative screen of FIG. 17 to allow users to choose different reports including an alarm report 122, a pressure ulcer (PU) status report 124, a usage report 126, and a history report 128.

Figure 22:
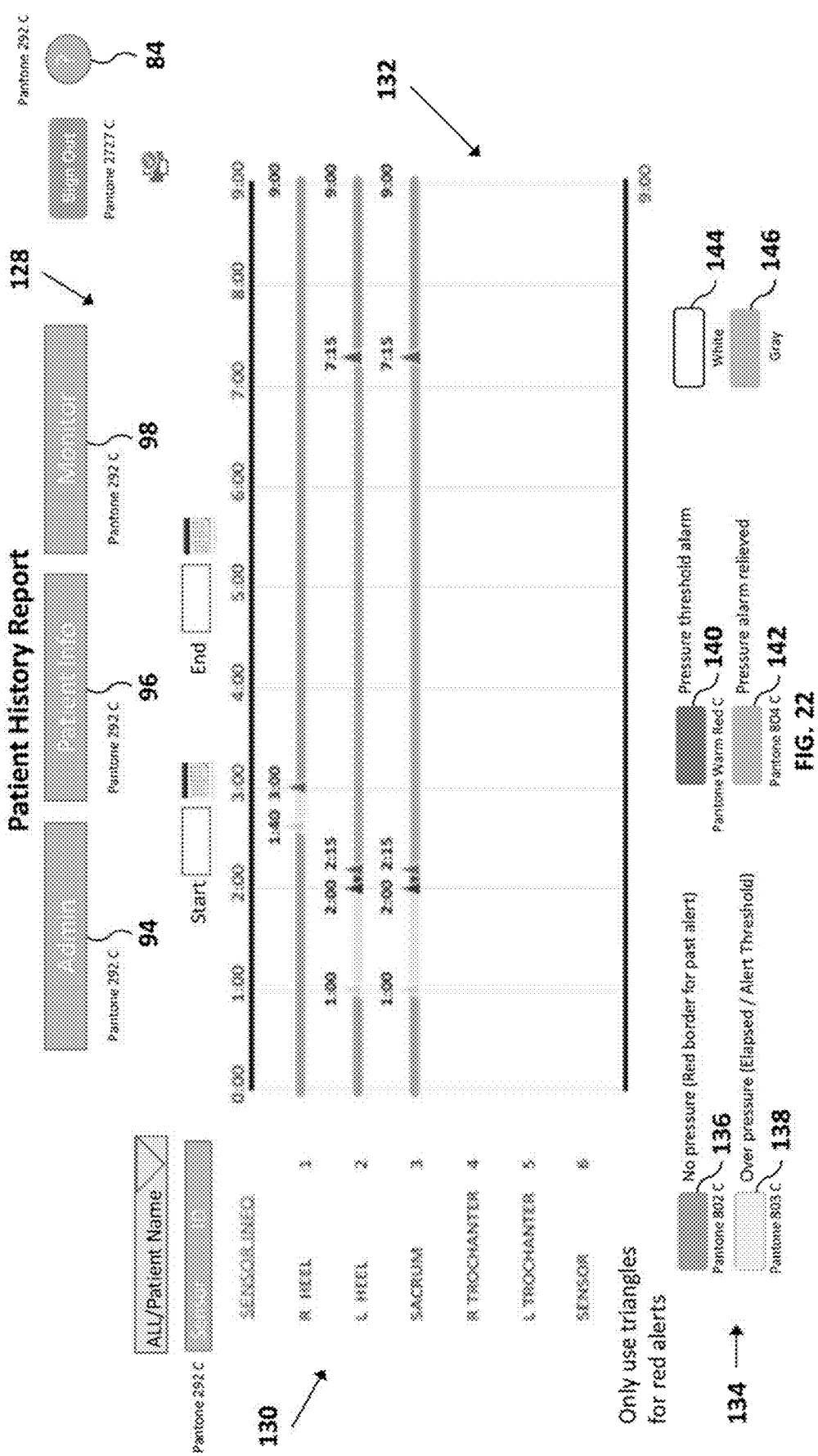
FIG. 22 represents an embodiment of a patient history report accessed through the reports module screen of FIG. 21.

FIG. 22 illustrates an example screen of the history report 128 that includes a listing of sensor descriptions 130 and a visual summary 132 associated with each sensor 30 displaying alerts based on time and pressure data. A set of visual status alerts 134 includes a no pressure status 136, an overpressure status 138, a pressure threshold alarm status 140, a pressure alarm relieved status 142, a low battery status 144, and a stopped sensor status 146.

Figure 23:
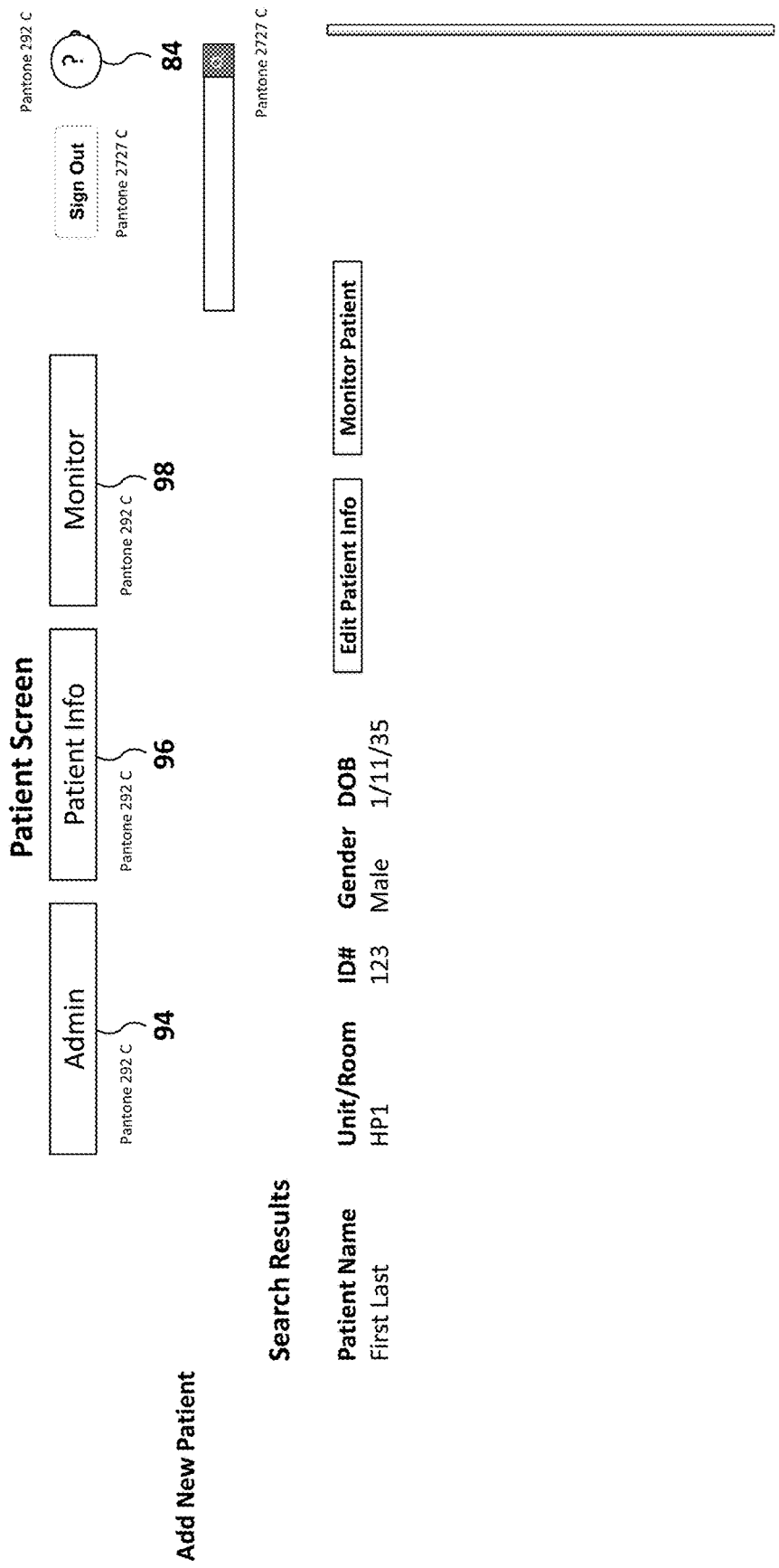
FIG. 23 represents an embodiment of a patient screen accessed through the patient information tab of the welcome screen of FIG. 16.

FIG. 23 illustrates a patient screen that can be accessed through the welcome screen 92 of FIG. 16 to allow users to add, change and delete patients in the system 10/58. The patient screen includes detailed patient information such as name, unit/room, ID #, gender, and date of birth.

If a user selects a particular patient after selecting the patient tab 96, the user lands on the patient detail screen illustrated in FIG. 24, which includes additional data such as patient weight, diagnosis, mobility, bed type, Braden, PURS (Pressure Ulcer Risk Scale), existing PUs, and new PUs. If a user selects an existing or new PU, FIG. 25 illustrates a PU status screen that includes dropdown menu options for specific PU status, location, stage/category, date and time.

Figure 26:
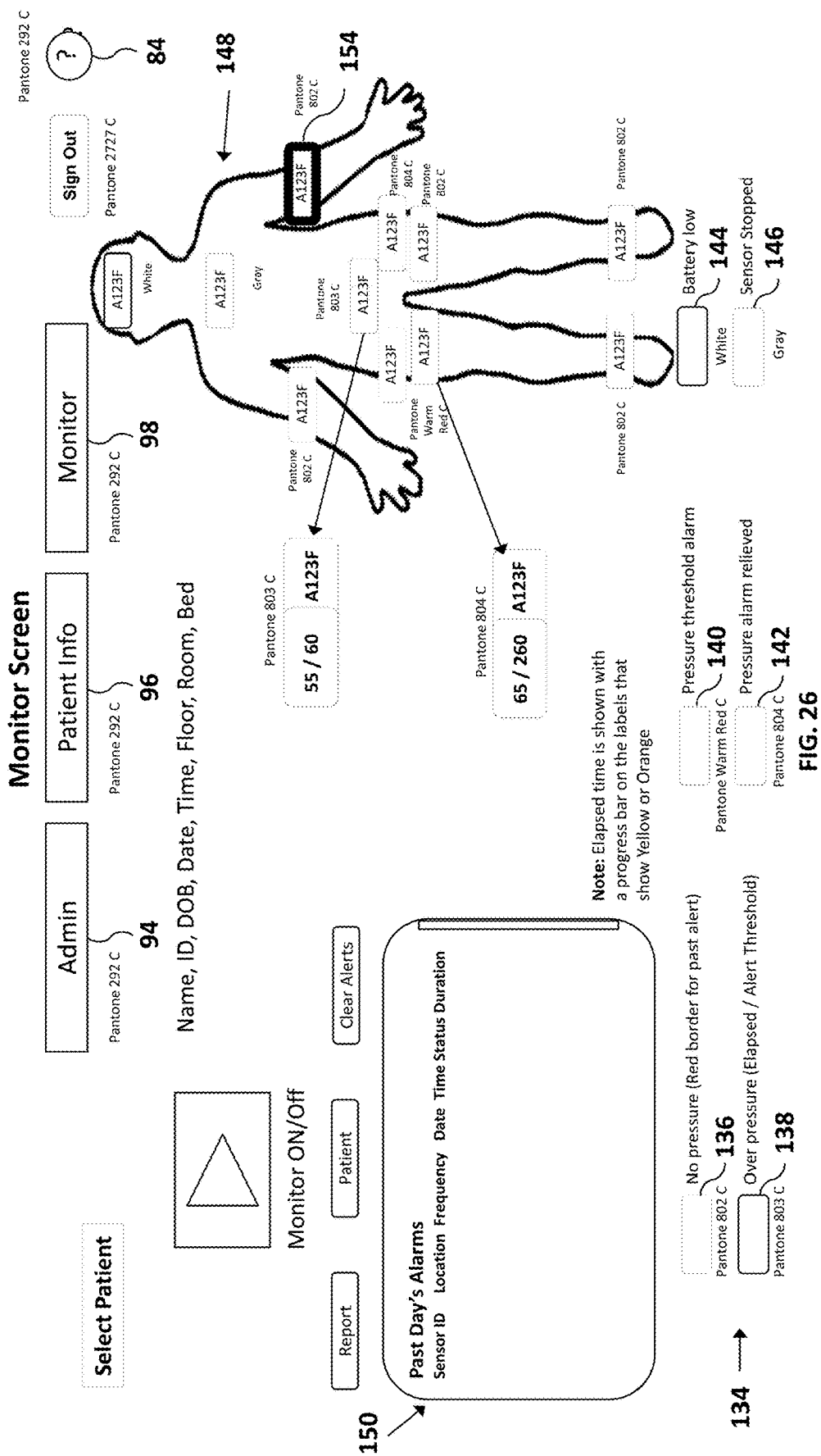
FIG. 26 represents an embodiment of a monitor screen accessed through the monitoring tab of the welcome screen of FIG. 16.

FIG. 26 illustrates the monitor user interface that can be accessed through the welcome screen 92 of FIG. 16 when the monitor tab 98 is selected. In particular, a visual indication of each sensor 30 and its location on the patient is illustrated on a human outline 148 in a patient sensor status window. The visual indication of each sensor 30 comprises a label 154 with information that identifies the sensor 30. As shown, each label 154 also incorporates an elapsed time progress bar, which may display elapsed time and warnings in the same manner as described for the progress bars 52 discussed in reference to FIGS. 5A and 5B. In particular, FIG. 26 indicates each label 154 as reflecting the sensor status discussed in reference to FIG. 22, namely, color-coded visual status alerts 134 that include a no pressure status 136, an overpressure status 138, a pressure threshold alarm status 140, a pressure alarm relieved status 142, a low battery status 144, and a stopped sensor status 146. An alarm history window 150 lists a history of past sensor alarms.

Figure 27:
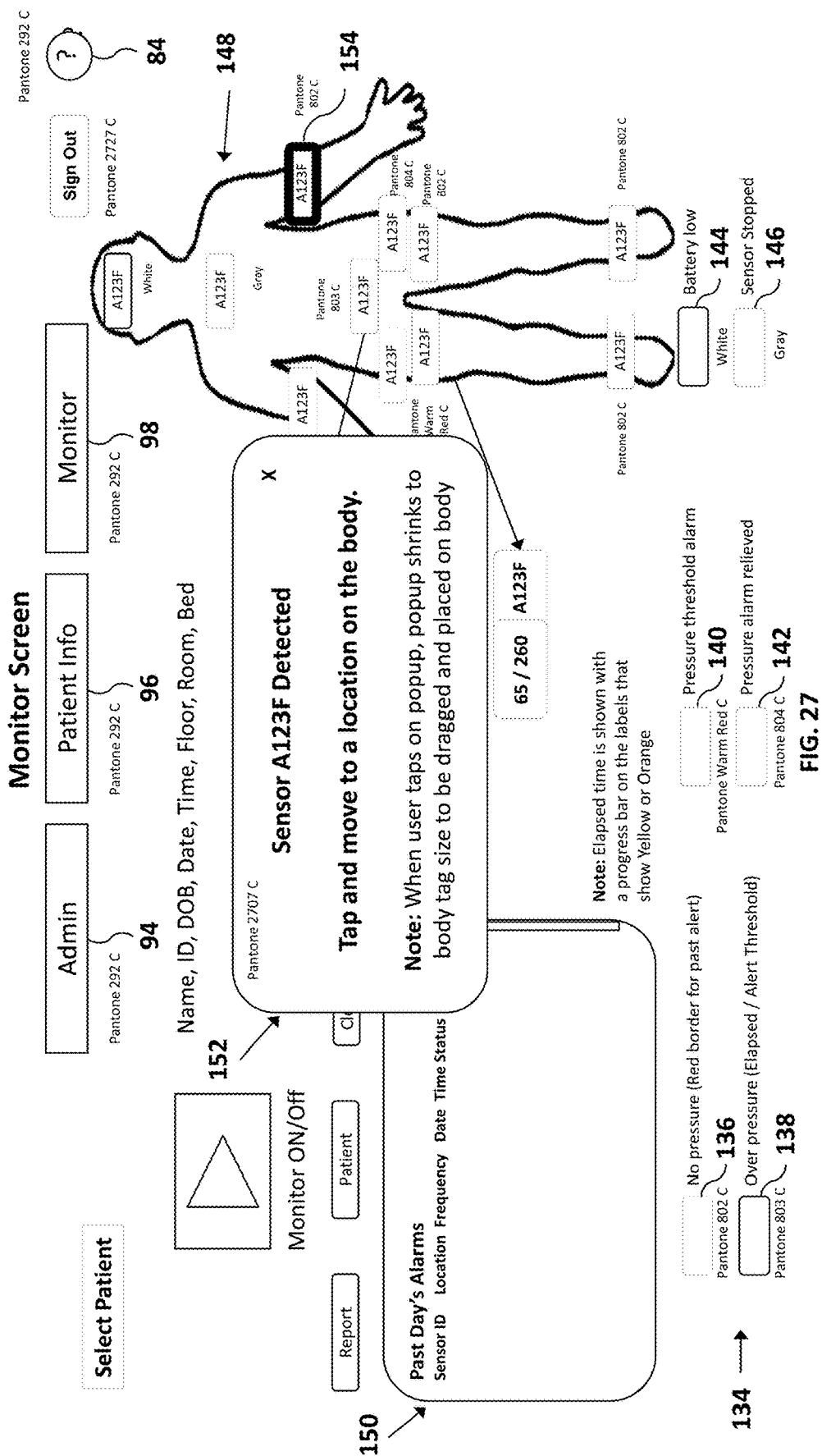
FIG. 27 represents an embodiment of automated sensor detection displayed on the monitor screen of FIG. 26.
Figure 28:
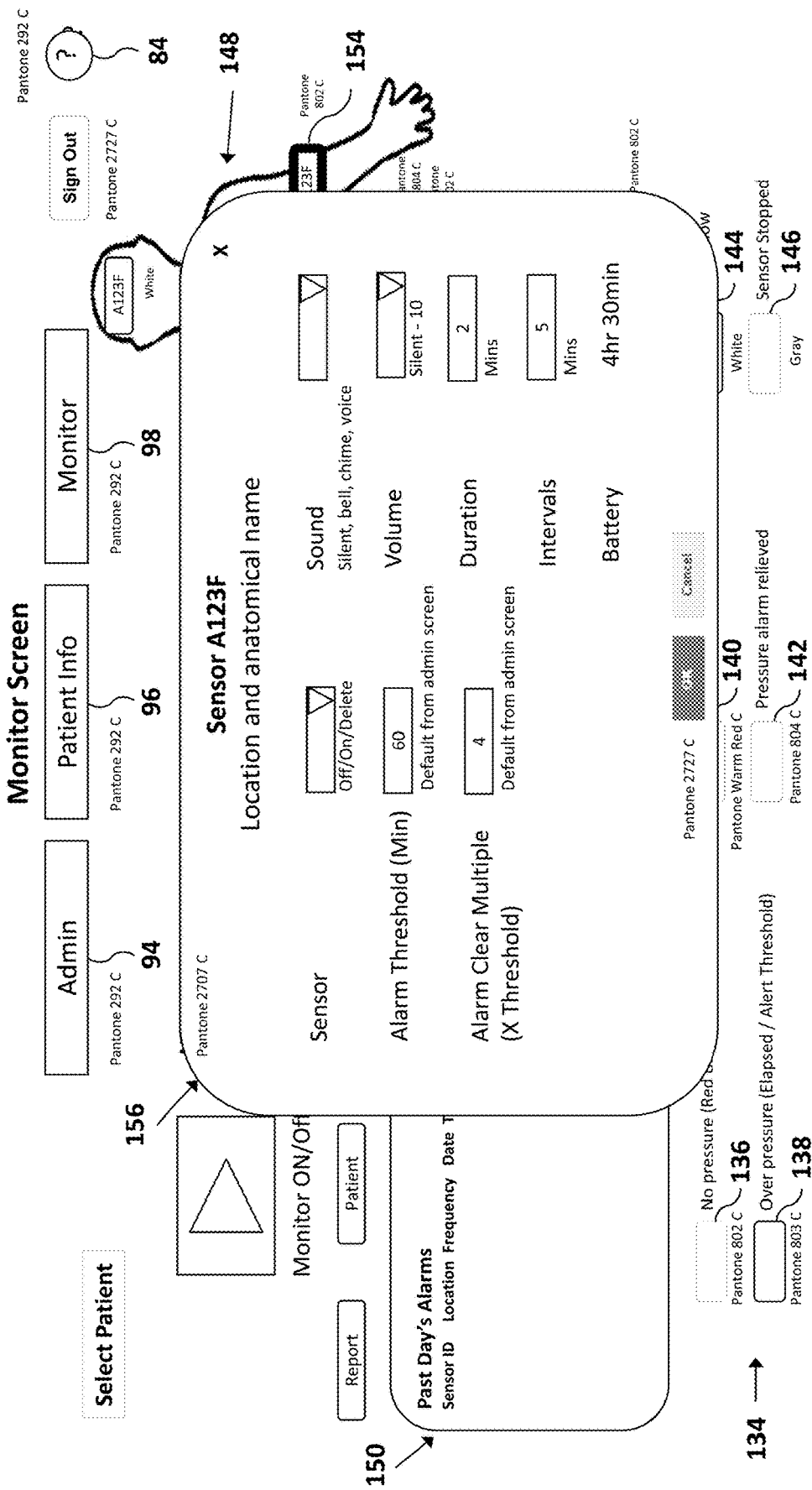
FIG. 28 represents an embodiment of automated sensor detection user-configurable variables displayed on the monitor screen of FIG. 26.

As illustrated in FIG. 27, a sensor detection window 152 is displayed when the tablet 13 is located near a sensor 30 and a button on the sensor 30 is depressed (not shown) to automatically detect the sensor 30. As illustrated in FIG. 28, if a user selects a sensor label 154 in the human outline 148, a sensor window 156 is displayed to allow the user to enter additional information on the sensor 30 and alarm thresholds. The sensor 30 can be registered using QR Codes to associate the particular sensor 30 with a patient and with part of that patient's body. For this purpose, the caregiver places the sensor 30 adjacent to the tablet 13 or the smartphone 68, which includes an application to read the QR label. In particular, the caregiver can use the smartphone 68 to take a picture of the QR label, which is read and processed by the application. The application then has a label with unique identification of the sensor 30. The user then drags the label 154 to a specific part of the body illustrated in the human outline 148 that serves as a visualization of the patient. When the user is done dragging the label 154 onto the part of the body of the patient, the user releases the button and the label 154 is associated with the part of the body where the label 154 is released.

Additional registration of the sensor 30 in the system 10/58 includes measuring the signal strength to detect the proximity of the sensor 30, a user pushing a button on the sensor 30 to initiate proximity detection of the sensor 30 so the sensor 30 can be registered in the system 10/58, or a user pushing the button in a unique sequence over a predefined period of time to initiate registration.

Figure 7:
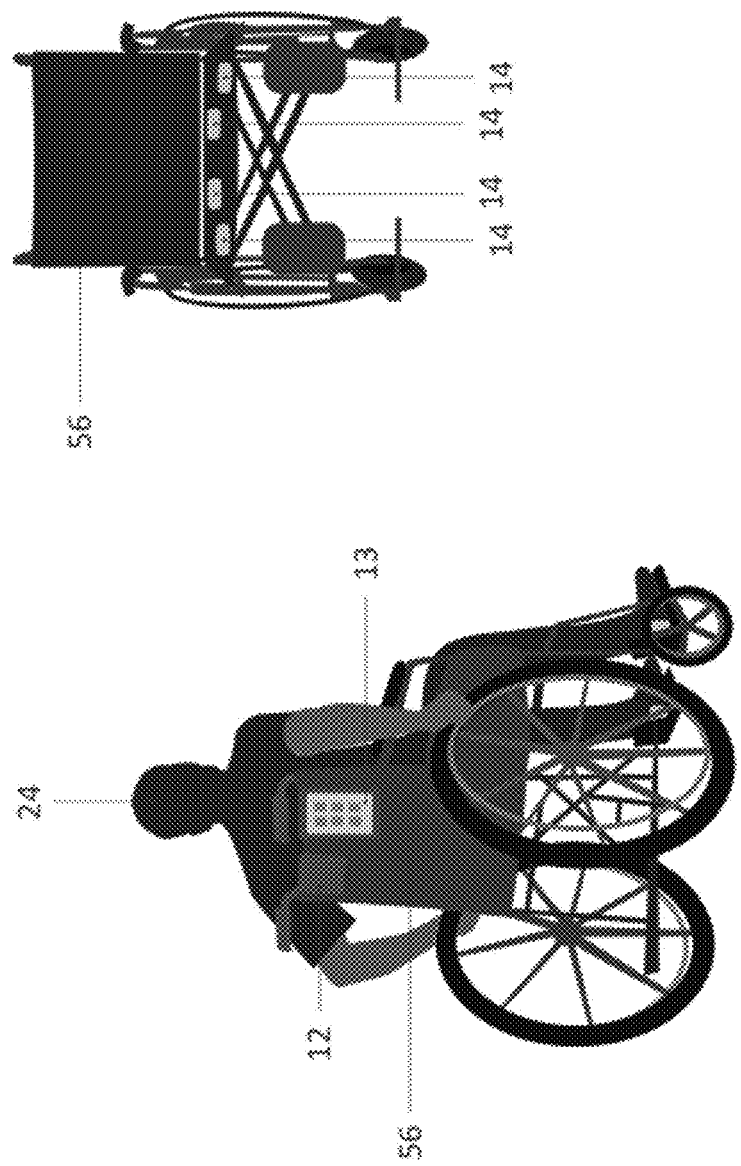
FIG. 7 represents a patient in a wheelchair being wirelessly monitored with the system of FIG. 1.

In addition to locating pressure sensing units 14 on a human body, it is foreseeable that the systems 10 and 58 may be used on other objects depending on the application. For example, it is also foreseeable that a sensing unit 14 could be incorporated into a prosthetic worn by a person to monitor pressure between the prosthetic and the person's skin contacted by the prosthetic, or located on or in a surface that a person will sit or lie on, such as wheelchairs, chairs, vehicle seats, bicycle seats, etc., or covers for such devices. Additionally, the sensing units 14 may be located in furniture, clothing, sporting equipment, or any other location where tracking pressure over a period of time is desirable. For example, FIG. 7 represents the system 10 being used with a wheelchair 56 and having pressure sensing units 14 located on or in a seat of the wheelchair 56.

The pressure monitoring systems 10 and 58 could be combined with other known types of sensors and transducers in order to provide a more comprehensive status of a patient. For example, the systems 10 and 58 may be configured to sense the patient's heart rate and/or blood pressure and transmit this information to the tablet 13 to be displayed with the pressure information. Alternatively, the software application of the tablet 13 may be configured to communicate with existing heart rate and/or blood pressure monitoring devices and incorporate this information into the display. In either case, the software application on the tablet 13 may be configured with preset limits for the patient's heart rate and/or blood pressure in substantially the same manner as described above relating to the pressure monitoring. As such, the software application may display a warning if the patient's heart rate or blood pressure drops below or exceeds the preset limits.

While the invention has been described in terms of specific embodiments, it is apparent that other forms could be adopted by one skilled in the art. For example, the pressure monitoring systems 10 and 58 and its components could differ in appearance and construction from the embodiment shown in the Figures, the functions of each component could be performed by components of different construction but capable of a similar (though not necessarily equivalent) function, and various materials and assembly, calibration and test procedures could be used in the manufacturing and setup of the systems 10 and 58. Other options include the use of different packaging, timer and pressure measurement modalities (including variable output pressure transducers), and the use of any number of pressure sensing units 14 and sensors 30, including different types of sensor technologies to measure a range of specific pressures. In addition, various different threshold pressure levels could be used, though a pressure level of 30 mmHg is currently universally accepted as a critical threshold pressure level in the development of pressure ulcers.

The system can also be configured for use by home patients and wheelchair patients, as well as for placement in the shoes of ambulatory patients to measure and warn against excess foot pressure-time. The system can also be adapted for use in treating pre-existing wounds and to incorporate wound care dressings into the pressure sensing units 14, for example, by impregnating a dressing layer of a pressure sensing unit 14 with topical antibiotics to aid in the treatment of bacterial infected wounds. The system may additionally include temperature sensors to detect if the skin is increasing the probability of a PU for alerting and time. Moisture sensors could detect if the skin is increasing the probability of a PU for alerting and time as well.

A variable pressure transducer could assist in relating a patient's weight and other health factors when configuring alerts and alarms. The system could also detect if a patient was out of the bed or a seat if all sensors are not reading any pressure. The system could further include skin capillary stimulation if the skin is increasing the probability of a PU for alerting and time. The system could detect softness and hardness of various beds and seats using a pressure sensor. A bed pad or chair pad could be embedded with sensors and time alerting, along with artificial limbs. The system could employ predictive analytics based on age, multi-sensor information and other metrics. Care of patients could be socialized to family members can remotely monitor the patients.

The system could further include a soil detection alert. Finally, a bacterial burden value could be calculated to alert a high probability of a PU. Accordingly, it should be understood that the invention is not limited to the specific embodiments illustrated in the Figures. It should also be understood that the phraseology and terminology employed above are for the purpose of disclosing the illustrated embodiments, and do not necessarily serve as limitations to the scope of the invention. Therefore, the scope of the invention is to be limited only by the following claims.

The invention claimed is:

1. A pressure monitoring system for providing a warning to a patient or caregiver that the patient should be moved to at least reduce a risk of soft tissue damage to the patient, the system comprising:
    a plurality of pressure sensing units, each pressure sensing unit adapted to be applied on or near a surface of the patient's body that is susceptible to damage from soft tissue pressure, each pressure sensing unit comprising a vibration device and at least one sensor configured to generate electrical outputs corresponding to soft tissue pressure sensed by the sensor at the surface of the patient's body;
    means for wirelessly monitoring a plurality of the electrical outputs generated by the sensors of the pressure sensing units;
    counters associated with the monitoring means and the sensors, each of the counters generating a separate counter value for a corresponding one of the sensors that increases from an initial value while the soft tissue pressure sensed by the corresponding sensor exceeds a predetermined pressure level and decreases toward the initial value while the soft tissue pressure sensed by the corresponding sensor does not exceed the predetermined pressure level;
    a display associated with the monitoring means that visually displays a human outline, visual indications of locations and identities of the sensors on the human outline, the counter values of the sensors, and a visual warning if the counter value of any of the sensors exceeds a predetermined counter value;
    means for generating an alarm while any of the counter values exceed the predetermined counter value; and
    wherein the vibration device of any one of the pressure sensing units is activated to vibrate to notify the patient of the alarm if both the counter value for a corresponding one of the sensors exceeds the predetermined counter value and the soft tissue pressure sensed by the corresponding one of the sensors exceeds the predetermined pressure level, and is deactivated once the soft tissue pressure is no longer sensed by the corresponding one of the sensors or no longer exceeds the predetermined pressure level.

2. The pressure monitoring system according to claim 1, wherein the counter values increase at a first ratio relative to actual elapsed time, the counter values decrease at a second ratio relative to actual elapsed time, and the second ratio is less than the first ratio.

3. The pressure monitoring system according to claim 1, wherein the visual warning comprises elapsed time progress bars that each increase and decrease with a corresponding one of the counter values.

4. The pressure monitoring system according to claim 1, wherein the sensors are adapted to generate the electrical outputs only if the soft tissue pressure exceeds the predetermined pressure level.

5. The pressure monitoring system according to claim 4, wherein the sensors generate the electrical outputs at an identical output level regardless of how much the soft tissue pressure exceeds the predetermined pressure level.

6. The pressure monitoring system according to claim 1, wherein the means for wirelessly monitoring the plurality of the electrical outputs generated by the sensors comprises a converter that is physically separate from the pressure sensing unit and is configured to wirelessly transmit the electrical outputs generated by the sensors to a device operating a software application thereon configured to interpret the electrical outputs to generate the counter.

7. The pressure monitoring system according to claim 1, wherein the sensors comprise multiple electrically-conductive dome sensors each comprising conductive circuitry that is electrically shorted if the predetermined pressure level is exceeded.

8. The pressure monitoring system according to claim 7, wherein at least one of the dome sensors is adapted to collapse and electrically short the conductive circuitry thereof if subjected to a collapsing force of at least forty grams.

9. The pressure monitoring system according to claim 1, wherein each of the pressure sensing unit further comprises a carrier, the carrier comprising a skin-side surface adapted to face the surface of the patient's body, a central aperture in which the sensor thereof is disposed, at least a first dressing layer that defines the skin-side surface of the carrier and in which the central aperture is not present so that the first dressing material is between the sensor and the surface of the patient's body, at least one foam layer in which the central aperture is defined and in which the sensor is disposed, and an adhesive strip that releasably overlies the central aperture, secures the sensor within the central aperture, and can be peeled back to allow replacement of the sensor in the central aperture.

10. The pressure monitoring system according to claim 1, wherein the alarm generating means comprises means for generating an audible warning if the counter value of any of the sensors is above the predetermined counter value and continuing to generate the audible warning until the soft tissue pressure sensed by the sensor drops below the predetermined pressure level.

11. The pressure monitoring system according to claim 1, wherein the alarm generating means comprises means for generating a notification that the counter value of any of the sensors previously exceeded the predetermined counter value, wherein the notification is continuously generated until disabled manually regardless of whether the counter value continues to exceed the predetermined counter value.

12. The pressure monitoring system according to claim 1, further comprising means for saving data regarding the counter and wirelessly uploading the data to a remote database.

13. The pressure monitoring system according to claim 1, further comprising a memory card on which are stored the soft tissue pressures and durations and alarm events of the monitoring system.

14. A pressure monitoring method using the pressure monitoring system according to claim 1 to warn the patient or the caregiver that the patient should be moved to at least reduce a risk of soft tissue damage to the patient, the method comprising:
- monitoring the plurality of the electrical outputs generated by the sensors over a preselected time period;
- continuously generating the alarm while any of the counter values value exceeds the predetermined counter value; and
- not generating the alarm if the counter values do not exceed the predetermined counter value.

\* \* \* \* \*